United States Patent
Wu et al.

(10) Patent No.: US 7,342,002 B2
(45) Date of Patent: Mar. 11, 2008

(54) MOLECULAR VACCINE LINKING AN ENDOPLASMIC CHAPERONE POLYPEPTIDE TO AN ANTIGEN

(75) Inventors: Tzyy-Choou Wu, Brookeville, MD (US); Chien-Fu Hung, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 308 days.

(21) Appl. No.: 10/343,448

(22) PCT Filed: Aug. 2, 2001

(86) PCT No.: PCT/US01/24134

§ 371 (c)(1),
(2), (4) Date: Aug. 4, 2003

(87) PCT Pub. No.: WO02/12281

PCT Pub. Date: Feb. 14, 2002

(65) Prior Publication Data

US 2005/0054820 A1   Mar. 10, 2005

Related U.S. Application Data

(60) Provisional application No. 60/222,902, filed on Aug. 3, 2000.

(51) Int. Cl.
*A61K 48/00*   (2006.01)
*C12N 15/63*   (2006.01)
*A01N 63/00*   (2006.01)

(52) U.S. Cl. .................... 514/44; 435/320.1; 424/93.1; 424/93.2; 424/93.21

(58) Field of Classification Search ..................... None
See application file for complete search history.

(56) References Cited

U.S. PATENT DOCUMENTS

| | | | |
|---|---|---|---|
| 5,834,309 A | 11/1998 | Thompson et al. | |
| 6,541,010 B1* | 4/2003 | Johnston et al. | 424/199.1 |
| 6,734,173 B1* | 5/2004 | Wu et al. | 514/44 |
| 2002/0091246 A1 | 7/2002 | Pardoll et al. | |
| 2004/0028693 A1 | 2/2004 | Wu et al. | |

(Continued)

FOREIGN PATENT DOCUMENTS

WO   WO 99 07860 A   2/1999

(Continued)

OTHER PUBLICATIONS

Liu et al, J Virol Mar. 2000;74:2888-94.*

(Continued)

*Primary Examiner*—Q. Janice Li
(74) *Attorney, Agent, or Firm*—Foley Hoag LLP

(57) ABSTRACT

This invention provides compositions and methods for inducing and enhancing immune responses, such as antigen-specific cytotoxic T lymphocyte (CTL) responses, using chimeric molecules comprising endoplasmic reticulum chaperone polypeptides and antigenic peptides. In particular, the invention provides compositions and methods for enhancing immune responses induced by polypeptides made in vivo by administered nucleic acid, such as naked DNA or expression vectors, encoding the chimeric molecules. The invention provides a method of inhibiting the growth of a tumor in an individual. The invention also provides novel self-replicating RNA virus constructs for enhancing immune responses induced by chimeric polypeptides made in vivo.

41 Claims, 9 Drawing Sheets

U.S. PATENT DOCUMENTS

| | | | |
|---|---|---|---|
| 2004/0086845 | A1 | 5/2004 | Wu et al. |
| 2005/0277605 | A1 | 12/2005 | Wu et al. |
| 2007/0026076 | A1 | 2/2007 | Wu et al. |

FOREIGN PATENT DOCUMENTS

| | | |
|---|---|---|
| WO | WO 99 65940 A | 12/1999 |
| WO | WO-01/29233 | 4/2001 |
| WO | WO-02/09645 | 2/2002 |
| WO | WO-02/12281 | 2/2002 |
| WO | WO-02/061113 | 8/2002 |
| WO | WO-03/085085 | 10/2003 |
| WO | WO-2004/098526 | 11/2004 |
| WO | WO-2005/047501 | 5/2005 |
| WO | WO-2005/081716 | 9/2005 |
| WO | WO-2006/073970 | 7/2006 |
| WO | WO-2006/081323 | 8/2006 |

OTHER PUBLICATIONS

Peng et al, Gene Ther 2006;13:67-77.*
Kerbel, Carcinogen 2000;21:505-15.*
Nawrocki et al, Cancer Treat Rev 1999;25:29-46.*
Nicchitta et al, Essays Biochem. 2000;36:15-25.*
Harris et al, J Immunol 1998;160:5404-9.*
Bennett et al, J Biol Chem 1998;273:23674-80.*
Eggleton et al (Scand J Immunol 1999;49:466-73.*
McCluskie et al, Mol Med May 1999;5:287-300.*
Torres et al, J Immunol 1997;158:4529-32.*
Nakano et al, J Virol 1997;71:7101-09.*
C-H Chen et al., "Enhancement of DNA Vaccine Potency By Linkage Of Antigen Gene To ANHSP70 Gene", Cancer Research, American Association For Cancer Research, vol. 60, pp. 1035-1042, (2000).
Sreyashi Basu et al., "Calreticulin, A Peptide-Binding Chaperone Of The Endoplasmic Reticulum, Elicits Tumor- And Peptide-Specific Immunity", Journal of Experimental Medicine, vol. 189(5):797-802, (1999).
Wolfgang Leitner et al., "DNA And RNA-Based Vaccines: Principles, Progress And Prospects", Vaccine, vol. 18(9-10):765-777, (1999).
Detlef Ockert et al., "Advances In Cancer Immunotherapy Symposium, Dresden, Germany", Immunology Today, vol. 20(2):63-65, (1999).
S. Nair et al., "Calreticulin Displays In Vivo Peptide-Binding Activity And Can Elicit CTL Responses Against Bound Peptides", Journal Of Immunology, vol. 162(11):6426-6432, (1999).
Cavill et al., "Generation of a Monoclonal Antibody Against Human Calreticulin by Immunization with a Recombinant Calreticulin Fusion Protein: Application in Paraffin-Embedded Sections," Appl. Immunohistochemistry & Molecular Morphology 7(2):150-155 (1999).
Chang, C-L. et al., "Control of human mesothelin-expressing tumors by DNA vaccines." Gene Therapy 1-10 (2007).
Chen, C-H. et al. "Recombinant DNA vaccines protect against tumors that are resistant to recombinant vaccinia vaccines containing the same gene." Gene Therapy 8:128-138 (2001).
Chen, C-H. et al., "Gene gun-mediated DNA vaccination induces antitumor immunity against human papillomavirus type 16 E7-expressing murine tumor metastases in the liver and lungs." Gene Therapy 6:1972-1981 (1999).
Chen, C-H. et al., "Boosting with recombinant vaccinia increases HPV-16 E7-specific T cell precursor frequencies of HPV-16 E7-expressing DNA vaccines," Vaccine 18:2015-2022 (2000).
Chen, C-H. et al., "Antigen-specific immunotherapy for human papillomavirus 16 E7-expressing tumors grown in the liver." Journal of Hepatology 33:91-98 (2000).
Chen et al., "Enhancement of DNA Vaccine Potency by Linkage of Antigen Gene to ANHSP70 Gene," Cancer Research, American Association for Cancer Research, 60:1035-1042 (2000).

Cheng, W-F. et al., "Cancer Immunotherapy Using Sindbis Virus Replicon Particles Encoding a VP22-Antigen Fusion." Human Gene Therapy. 13:553-568 (2002).
Cheng, W-F. et al. "Enhancement of Sindbis Virus Self-Replicating RNA Vaccine Potency by Linkage of Herpes Simplex Virus Type 1 VP22 Protein to Antigen." Journal Of Virology, 75(5): 2368-2376 (2001).
Cheng, W-F. et al. "Enhancement of Sindbis Virus Self-Replicating RNA Vaccine Potency by Linkage of Mycobacterium tuberculosis Heat Shock Protein 70 Gene to an Antigen Gene." Journal of Immunology, 166:6218-6226 (2001).
Cheng, W-F. et al., "Tumor-specific immunity and antiangiogenesis generated by a DNA vaccine encoding calreticulin linked to a tumor antigen." J. Clin. Invest. 108:669-678 (2001).
Cheng, W-F. et al. "Enhancement of Sindbis Virus Self-Replicating RNA Vaccine Potency by Targeting Antigen to Endosomal/Lysosomal Compartments." Human Gene Therapy 12:235-252 (2001).
Chavin, K. et al., "Obesity Induces Expression of Uncoupling Protein-2 in Hepatocytes and Promotes Liver ATP Depletion." J. Biol. Chem. 274(9):5692-5700 (1999).
Cheng, W-F. et al., "Repeated DNA Vaccinations Elicited Qualitatively Different Cytotoxic T Lymphocytes and Improved Protective Antitumor Effects." J Biomed Sci 9:675-687 (2002).
Cheng, W. et al., "CD8+ T cells, NK cells and IFN-γ are Important for control of tumor with downregulated MHC class I expression by DNA vaccination." Gene Therapy 10:1311-1320, (2003).
Devaraj, K. et al., "Development of HPV Vaccines for HPV-Associated Head and Neck Squamous Cell Carcinoma," Crit. Rev. Oral Biol. Med. 14(5):345-362, (2003).
Heller, J. et al., "Tetra-O-methyl Nordihydroguaiaretic Acid Induces G2 Arrest in Mammalian Cells and Exhibits Tumoricidal Activity in Vivo," Cancer Research 61:5499-5504, (2001).
Hsieh, C-J. et al., "Ehnancement of vaccinia vaccine potency by linkage of tumor antigen gene to gene encoding calreticulin." Vaccine 22:3993-4001. (2004).
Huang, C-C. et al., "HPV In Situ Hybridization With Catalyzed Signal Amplification And Polymerase Chain Reaction In Establishing Cerebellar Metastasis Of A Cervical Carcinoma." Human Pathology, 30(5):587-591. (1999).
Huang, C-H. et al. "Cancer Immunotherapy using a DNA vaccine encoding a single-chain trimer of MHC class I linked to an HPV-16 E6 immunodominant CTL epitope." Gene Therapy. 12:1180-1186 (2005).
Hung, C-F. et al., "Cancer Immunotherapy Using a DNA Vaccine Encoding the Translocation Domain of a Bacterial Toxin Linked to a Tumor Antigen." Cancer Research 61: 3698-3703 (2001).
Hung, C-F. et al., "Enhancement of DNA Vaccine Potency by Linkage of Antigen Gene to a Gene Encoding the Extracellular Domain of Fms-like Tyrosine Kinase 3-Ligand." Cancer Research 61:1080-1088, (2001).
Hung, C-F., et al., "Improving DNA Vaccine Potency by Linking Marek's Disease Virus Type 1 VP22 to an Antigen," Journal Of Virology, 76(6):2676-2682 (2002).
Hung, C-F. et al., "Improving DNA vaccine potency via modification of preofessional antigen presenting cells." Current Opinion in Molecular Therapeutics, 5(1):20-24 (2003).
Hung, C-F. et al., "Enhancing Major Histocompatibility Complex Class I Antigen Presentation by Targeting Antigen to Centrosomes," Cancer Research. 63: 2393-2398, (2003).
Hung, C-F. et al., "Control of mesothelin-expressing ovarian cancer using adoptive transfer of mesothelin peptide-specific CD8+ T cells." Gene Therapy, pp. 1-9 (2007).
Hung, C-F. et al., "DNA Vaccines Encoding Ii-PADRE Generates Potent PADRE-specific CD4+ T-Cell Immune Responses and Enhances Vaccine Potency." Mol. Ther. 15(6):1211-9. (2007).
Hung, C-F. et al., Methods in Molecular Medicine, vol. 127: DNA Vaccines: Methods and Protocols: Second Edition. Edited by Saltzman et al. Humana Press Inc., Totowa, NJ.
Hung, C-F. et al. "A DNA vaccine encoding a single-chain trimer HLA-A2 linked to human mesothelin peptide generates anti-tumor effects against human mesothelin-expressing tumors." Vaccine 25:127-135 (2007).

Hung, C-F. et al., "Vaccinia virus preferentially infects and controls human and murine ovarian tumors in mice." Gene Therapy. 14:20-29 (2007).

Ji, H et al., "Targeting Human Papillomavirus Type 16 E7 to the Endosomal/Lysosomal Compartment Enhances the Antitumor Immunity of DNA Vaccines against Murine Human Papillomavirus Type 16 E7-Expressing Tumors," Human Gene Therapy 10:2727-2740 (1999).

Ji, H et al., "Antigen-Specific Immunotherapy For Murine Lung Metastatic Tumors Expressing Human Papillomavirus Type 16 E7 Oncoprotein." Int. J. Cancer: 78, 41-45 (1998).

Kadkol, S. et al., Chapter 5: In Situ Hybridization in Cancer and Normal Tissue. Methods in Molecular Biology, vol. 223: Tumor Suppressor Genes, vol. II, Edited by W. El-Deiry, Humana Press Inc., Totowa, NJ., 2003.

Kang, T. et al., "Enhancing dendritic cell vaccine potency by combining a BAK/BAX siRNA-mediated antiapoptotic strategy to prolong dendritic cell life with an intracellular strategy to target antigen to lysosomal compartments." Int. J. Cance, 120:1696-1703 (2007).

Kim, D. et al., "Monitoring the Trafficking of Adoptively Transferred Antigen-Specific CD8-Positive T Cells In Vivo, Using Noninvasive Luminescence Imaging." Human Gene Therapy. 18:1-14 (2007).

Kim, T. et al., Enhancing DNA vaccine potency by coadministration of DNA encoding antiapoptotic proteins. J. Clin. Invest. 112:109-117 (2003).

Kim, T. et al., "Enhancing DNA Vaccine Potency by Combining a Strategy to Prolong Dendritic Cell Life with Intracellular Targeting Strategies." The Journal of Immunology, 171:2970-2976, (2003).

Kim, T. et al., "DNA Vaccines Employing Intracellular Targeting Strategies and a Strategy to Prolong Dendritic Cell Life Generate a Higher Number of CD8+ Memory T Cells and Better Long-Term Antitumor Effects Compared with a DNA Prime-Vaccinia Boost Regimin." Human Gene Therapy 16:26-34 (2005).

Kim, T. et al. "Modification of Professional Antigen-Presenting Cells with Small Interfering RNA In vivo to Enhance Cancer Vaccine Potency." Cancer Res. 65(1):309-316. 2005.

Kim, T. et al., "A DNA Vaccine Co-Expressing Antigen and an Anti-Apoptotic Molecule Further Enhances the Antigen-Specific CD8+ T-Cell Immune Response." J. Biomed. Sci. 11:493-499 (2004).

Kim, T. et al., "Generation and Characterization of DNA Vaccines Targeting the Nucleocapsid Protein of Severe Acute Respiratory Syndrome Caronavirus." Journal of Virology, 78(9):4638-4645. (2004).

Kim, T. et al., "Vaccination with a DNA Vaccine Encoding Herpes Simplex Type 1 VP22 Linked to Antigen Generates Long-Term Antigen-Specific CD8-Positive memory T Cells and Protective Immunity." Human Gene Therapy. 15:167-177. (2004).

Kim, J. et al., "Comparison of HPV DNA vaccines employing intracellular targeting strategies." Gene Therapy, 11:1011-1018 (2004).

Kim, T. et al., "Enhancement of suicidal DNA vaccine potency by delaying suicidal DNA-Induced cell death." Gene Therapy. 11:336-342. (2004).

Kim, T. et al., "Enhancement of DNA Vaccine Potency by Coadministration of a Tumor Antigen Gene and DNA Encoding Serine Protease Inhibitor-6." Cancer Research. 64:400-405 (2004).

Lafond-Walker, A. et al., "Inducible Nitric Oxide Synthase Expression in Coronary Arteries of Transplanted Human Hearts with Accelerated Graft Arteriosclerosis." American Journal of Pathology, 151(4): 919-925 (1997).

Liaw, K. et al., "Human papillomavirus and cervical neoplasia: a case-control study in Taiwan." Int. J. Cancer. 62(5):565-71 (1995).

Lin, K-Y. et al., "Ectopic Expression of Vascular Cell Adhesion Molecule-1 as a New Mechanism for Tumor Immune Evasion." Cancer. Res. 67(4):1832-1841 (2007).

Lin, C-T. et al., "Boosting with Recombinant Vaccinia Increases HPV-16 E7-Specific T Cell Precursor Frequencies and Antitumor Effects of HPV-16 E7-Expressing Sindbis Virus Replicon Particles." Molecular Therapy. 8(4):559-566 (2003).

Lin, K-Y. et al., "Treatment of Established Tumors with a Novel Vaccine That Enhances Major Histocompatibility Class II Presentation of Tumor Antigen." Cancer Research 56:21-26 (1996).

Lin, Y-Y. et al., "Vaccines against human papillomavirus." Frontiers in Bioscience. 12:246-264 (2007).

Lin, Ken-Yu et al., "Coinfection of HPV-11 and HPV-16 in a case of Laryngeal Squamous Papillomas With severe Dysplasia." Laryngoscope. 107(7):942-947 (1997).

Ling, M. et al., "Preventive and Therapeutic Vaccines for Human Papillomavirus-Associated Cervical Cancers." J Biomed Sci 7:341-356 (2000).

Mao, C-P. et al., "Immunological research using RNA interference technology." Immunology, 121:295-307 (2007).

Mao, C-P. et al. "Immunotherapeutic strategies employing RNA interference technology for the control of cancers." Journal of Biomedical Science 14:15-29 (2007).

Mold, D. et al., "Four Classes of HERV-K Long Terminal Repeats and Their Relative Promoter Strengths for Transcription." J Biomed Sci 4:78-82 (1997).

Moniz, M. et al., "HPV DNA Vaccines," Frontiers in Bioscience 8, d55-68, (2003).

Pai, S I et al., "Prospects of RNA Interference therapy for cancer." Gene Therapy. 13:464-477 (2006).

Peng, S. et a., "HLA-DQB1*02- restricted HPV-16 E7 Peptide-Specific CD4+ T-Cell Immune Responses Correlate with Regression of HPV-16-Associated High-Grade Squamous Intraepithelial Lesions." Clin. Cancer Res. 13(8):2479-2487 (2007).

Peng, S, et al., "A combination of DNA vaccines targeting human papillomavirus type 16 E6 and E7 generates potent antitumor effects." Gene Therapy. 13:257-265 (2006).

Peng, S. et al., "Vaccination with Dendritic Cells Transgected with BAK and BAX siRNA Enhances Antigen-Specific Immune Responses by Prolonging Dendritic Cell Life." Human Gene Therapy 16:584-593 (2005).

Huanh, C-C. et al., "Generation of Type-Specific Probes for the Detection of Single-Copy Human Papillomavirus by a Novel In Situ Hybridization Method." Mod. Pathol. 11(10):971-977 (1998).

Peng, S. et al., "Development of a DNA Vaccine targeting Human Papillomavirus Type 16 Oncoprotein E6." Journal of Virology. 78(16):8468-8476. (2004).

Roden, R. et al. "The impact of preventative HPV Vaccination." Discovery Medicine. vol. 6, No. 35, pp. 175-181 (2006).

Roden, R. et al., "Vaccination to Prevent and Treat Cervical Cancer." Human Pathology. 35(8): 971-982. (2004).

Roden and Wu. "How will HPV vaccines affect cervical cancer?" Nature Reviews. 6:753-763. (2006).

Shalinsky et al., "Marked Antiangiogenic and Antitumor Efficacy of AG3340 in Chemoresistant Human Non-Small Cell Lung Cancer Tumors: Single Agent and Combination Chemotherapy Studies," Clinical Cancer Research 5:1905-1917 (1999).

Tomson, T. et al. "Human papillomavirus vaccines for the prevention and treatment of cervical cancer." Current Opinion in Investigational Drugs, 5(12):1247-1261. (2004).

Trimble, C, et al., "Spontaneous Regression of High-Grade Cervical Dysplasia: Effects of Human Papillomavirus Type and HLA Phenotype." Clin. Cancer Res. 11(13):4717-4723 (2005).

Trimble, C. et al., "Comparison of the CD8+ T cell responses and antitumor effects generated by DNA vaccine administered through gen gun, biojector and syringe." Vaccine. 21:4036-4042, (2003).

Trompeter, Hans-Ingo et al., "Variable Nuclear Cytoplasmic Distribution of the 11.5-kDa Zinc-binding Protein (Parathymosin-α) and Identification of a Bipartite Nuclear Localization Signal," The Journal of Biological Chemistry 271(2):1187-1193 (1996).

Ramos-Soriano, A. et al., "Enteric pathogens associated with gastrointestinal dysfunction in children with HIV infection." Molecular and Cellular Probes 10, 67-73 (1996).

Rashid, A. et al., "Mitochondrial Proteins That Regulate Apoptosis and Necrosis Are Induced in Mouse Fatty Liver." Hepatology 29:1131-1138 (1999).

Trujillo, J. et al., "Characterization of human papillomavirus type 57b: transforming activity and comparative sequence analysis as probes for biological determinants associated with high-risk oncogenic viruses." Virus genes. 12(2):165-78 (1996).

Tsu, K-F. et al., "Enhancement of suicidal DNA vaccine potency by linking Mycobacterium tuberculosis heat shock protein 70 to an antigen." Gene Therapy 8, 376-383 (2001).

Vu, K. et al., "Cellular Proliferation, Estrogen Receptor, Progesterone Receptor, and bcl-2 Expression in GnRH Agonist-Treated Uterine Leiomyomas." Human Pathology 29:359-363 (1998).

Wang, T-L. et al., "Intramuscular administration of E7-transfected dendritic cells generates the most potent E7-specific anti-tumor immunity." Gene Therapy 7:726-733 (2000).

Wu, T-C, et al., "Engineering an intracellular pathway for major histocompatibility complex class II presentation of antigens." Proc. Natl. Acad. Sci. 92:11671-11675 (1995).

Wu, T-C. "Therapeutic human papillomavirus DNA vaccination strategies to control cervical cancer." European Journal of immunology. 37:310-314 (2007).

Wu, T-C. et al., "A Reassessment of The Role of B7-1 Expression in Tumor Rejection." J. Exp. Med. 182:1415-1421 (1995).

Wu, T-C. et al., "Demonstration of human papillomavirus (HPV) genomic amplification and viral-like particles from CaSki cell line in SCID mice." Journal of Virological Methods 65:287-298 (1997).

Wu, T-C. et al., "Detection of the Human Cytomegalovirus 2.0-kb Immediate Early Gene I Transcripts in Permissive and Nonpermissive Infections by RNA in situ Hybridization." J Biomed Sci 4:19-27 (1997).

Yen, M. et al., "Diffuse Mesothelin Expression Correlates with Prolonged Patient Survival in Ovarian Serous Carcinoma." Clin. Cancer. Res. 12(3):827-831 (2006).

W.-F. Cheng, C.-F. Hung, C.-A. Chen, C.-N. Lee, Y.-N. Su, C.-Y. Chai, D. A. K. Boyd, C.-Y. Hsieh and T.-C. Wu (2005) Characterization of DNA Vaccines Encoding the Domains of Calreticulin for Their Ability to Elicit Tumor-Specific Immunity and Antiangiogenesis Vaccine 23: 3864-3874.

S. Peng, T.T. Tomson, C. Trimble, H. Ji, L. He, Y.-C. Tsai, B. Macaes, C.-F. Hung and T.-C. Wu (2005) Characterization of HPV16-E6 DNA vaccines employing intracellular targeting and intercellular spreading strategies. Journal of Biomedical Science. 12: 689-700.

\* cited by examiner

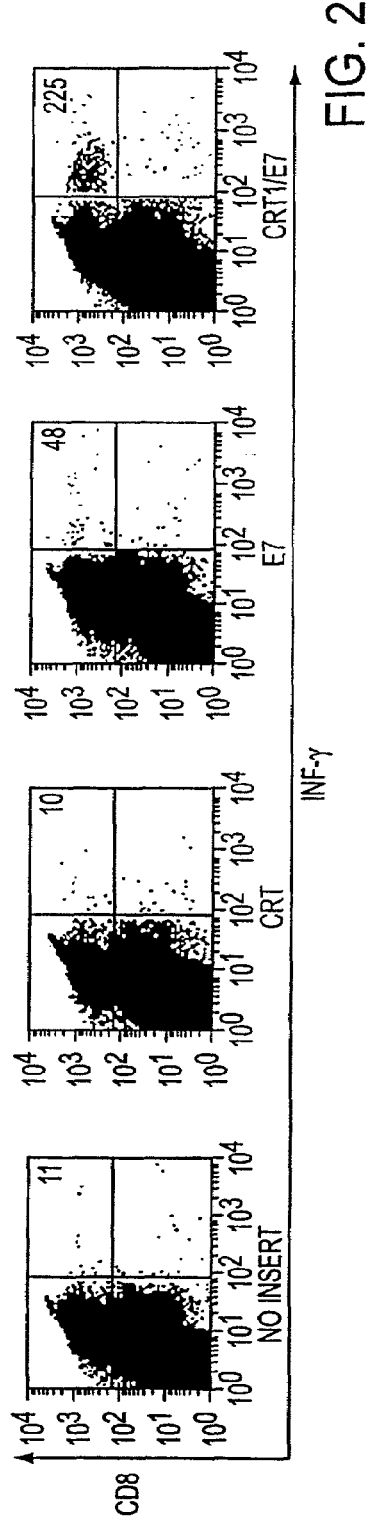
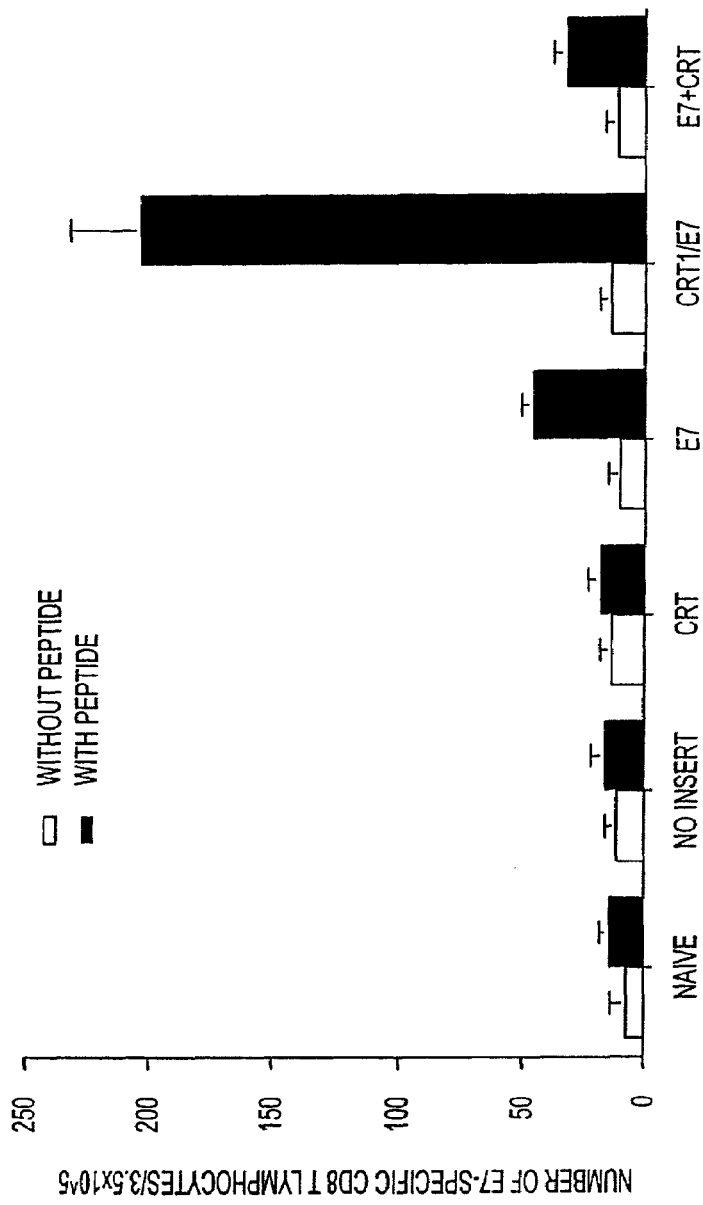

DNA CONSTRUCTS
SINrep5 
SINrep5-HSP70 
SINrep5-E7 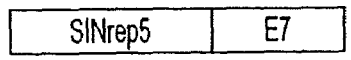
SIN5rep5-E7/HSP70 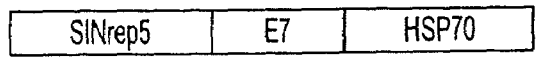
RNA TRANSCRIPTS
SINrep5 
SINrep5-HSP70 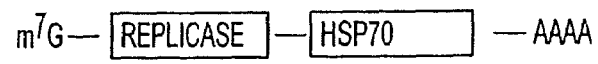
SINrep5-E7 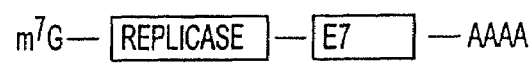
SIN5rep5-E7/HSP70 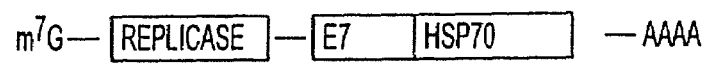
FIG. 9

SEQUENCE LISTING

```
<160> NUMBER OF SEQ ID NOS: 7

<210> SEQ ID NO 1
<211> LENGTH: 1899
<212> TYPE: DNA
<213> ORGANISM: Homo sapiens
<220> FEATURE:
<221> NAME/KEY: CDS
<222> LOCATION: (69)..(1319)
<223> OTHER INFORMATION:

<400> SEQUENCE: 1
gtccgtactg cagagccgct gccggagggt cgttttaaag ggccgcgttg ccgcccctc         60 ggcccgcc atg ctg cta tcc gtg ccg ctg ctg ctc ggc ctc ctc ggc ctg       110
         Met Leu Leu Ser Val Pro Leu Leu Leu Gly Leu Leu Gly Leu
         1               5                  10 gcc gtc gcc gag ccc gcc gtc tac ttc aag gag cag ttt ctg gac gga        158
Ala Val Ala Glu Pro Ala Val Tyr Phe Lys Glu Gln Phe Leu Asp Gly
15                  20                  25                  30 gac ggg tgg act tcc cgc tgg atc gaa tcc aaa cac aag tca gat ttt        206
Asp Gly Trp Thr Ser Arg Trp Ile Glu Ser Lys His Lys Ser Asp Phe
                35                  40                  45 ggc aaa ttc gtt ctc agt tcc ggc aag ttc tac ggt gac gag gag aaa        254
Gly Lys Phe Val Leu Ser Ser Gly Lys Phe Tyr Gly Asp Glu Glu Lys
            50                  55                  60 gat aaa ggt ttg cag aca agc cag gat gca cgc ttt tat gct ctg tcg        302
Asp Lys Gly Leu Gln Thr Ser Gln Asp Ala Arg Phe Tyr Ala Leu Ser
        65                  70                  75 gcc agt ttc gag cct ttc agc aac aaa ggc cag acg ctg gtg gtg cag        350
```

```
Ala Ser Phe Glu Pro Phe Ser Asn Lys Gly Gln Thr Leu Val Val Gln
         80              85                  90 ttc acg gtg aaa cat gag cag aac atc gac tgt ggg ggc ggc tat gtg     398
Phe Thr Val Lys His Glu Gln Asn Ile Asp Cys Gly Gly Gly Tyr Val
 95              100                 105                 110 aag ctg ttt cct aat agt ttg gac cag aca gac atg cac gga gac tca     446
Lys Leu Phe Pro Asn Ser Leu Asp Gln Thr Asp Met His Gly Asp Ser
                 115                 120                 125 gaa tac aac atc atg ttt ggt ccc gac atc tgt ggc cct ggc acc aag     494
Glu Tyr Asn Ile Met Phe Gly Pro Asp Ile Cys Gly Pro Gly Thr Lys
                 130                 135                 140 aag gtt cat gtc atc ttc aac tac aag ggc aag aac gtg ctg atc aac     542
Lys Val His Val Ile Phe Asn Tyr Lys Gly Lys Asn Val Leu Ile Asn
             145                 150                 155 aag gac atc cgt tgc aag gat gat gag ttt aca cac ctg tac aca ctg     590
Lys Asp Ile Arg Cys Lys Asp Asp Glu Phe Thr His Leu Tyr Thr Leu
         160                 165                 170 att gtg cgg cca gac aac acc tat gag gtg aag att gac aac agc cag     638
Ile Val Arg Pro Asp Asn Thr Tyr Glu Val Lys Ile Asp Asn Ser Gln
175             180                 185                 190 gtg gag tcc ggc tcc ttg gaa gac gat tgg gac ttc ctg cca ccc aag     686
Val Glu Ser Gly Ser Leu Glu Asp Asp Trp Asp Phe Leu Pro Pro Lys
                 195                 200                 205 aag ata aag gat cct gat gct tca aaa ccg gaa gac tgg gat gag cgg     734
Lys Ile Lys Asp Pro Asp Ala Ser Lys Pro Glu Asp Trp Asp Glu Arg
             210                 215                 220 gcc aag atc gat gat ccc aca gac tcc aag cct gag gac tgg gac aag     782
Ala Lys Ile Asp Asp Pro Thr Asp Ser Lys Pro Glu Asp Trp Asp Lys
         225                 230                 235 ccc gag cat atc cct gac cct gat gct aag aag ccc gag gac tgg gat     830
Pro Glu His Ile Pro Asp Pro Asp Ala Lys Lys Pro Glu Asp Trp Asp
     240                 245                 250 gaa gag atg gac gga gag tgg gaa ccc cca gtg att cag aac cct gag     878
Glu Glu Met Asp Gly Glu Trp Glu Pro Pro Val Ile Gln Asn Pro Glu
255                 260                 265                 270 tac aag ggt gag tgg aag ccc cgg cag atc gac aac cca gat tac aag     926
Tyr Lys Gly Glu Trp Lys Pro Arg Gln Ile Asp Asn Pro Asp Tyr Lys
                 275                 280                 285 ggc act tgg atc cac cca gaa att gac aac ccc gag tat tct ccc gat     974
Gly Thr Trp Ile His Pro Glu Ile Asp Asn Pro Glu Tyr Ser Pro Asp
             290                 295                 300 ccc agt atc tat gcc tat gat aac ttt ggc gtg ctg ggc ctg gac ctc     1022
Pro Ser Ile Tyr Ala Tyr Asp Asn Phe Gly Val Leu Gly Leu Asp Leu
         305                 310                 315 tgg cag gtc aag tct ggc acc atc ttt gac aac ttc ctc atc acc aac     1070
Trp Gln Val Lys Ser Gly Thr Ile Phe Asp Asn Phe Leu Ile Thr Asn
     320                 325                 330 gat gag gca tac gct gag gag ttt ggc aac gag acg tgg ggc gta aca     1118
Asp Glu Ala Tyr Ala Glu Glu Phe Gly Asn Glu Thr Trp Gly Val Thr
335                 340                 345                 350 aag gca gca gag aaa caa atg aag gac aaa cag gac gag gag cag agg     1166
Lys Ala Ala Glu Lys Gln Met Lys Asp Lys Gln Asp Glu Glu Gln Arg
                 355                 360                 365 ctt aag gag gag gaa gaa gac aag aaa cgc aaa gag gag gag gag gca     1214
Leu Lys Glu Glu Glu Glu Asp Lys Lys Arg Lys Glu Glu Glu Glu Ala
             370                 375                 380 gag gac aag gag gat gat gag gac aaa gat gag gat gag gag gat gag     1262
Glu Asp Lys Glu Asp Asp Glu Asp Lys Asp Glu Asp Glu Glu Asp Glu
         385                 390                 395
```

-continued

```
gag gac aag gag gaa gat gag gag gaa gat gtc ccc ggc cag gcc aag    1310
Glu Asp Lys Glu Glu Asp Glu Glu Asp Val Pro Gly Gln Ala Lys
    400                 405                 410 gac gag ctg tagagaggcc tgcctccagg gctggactga ggcctgagcg            1359
Asp Glu Leu
415 ctcctgccgc agagcttgcc gcgccaaata atgtctctgt gagactcgag aactttcatt  1419
tttttccagg ctggttcgga tttggggtgg attttggttt tgttcccctc ctccactctc  1479
ccccacccccc tccccgccct ttttttttt tttttaaac tggtatttta tcctttgatt   1539
ctccttcagc cctcacccct ggttctcatc tttcttgatc aacatctttt cttgcctctg  1599
tgccccttct ctcatctctt agctcccctc caacctgggg ggcagtggtg tggagaagcc  1659
acaggcctga gatttcatct gctctccttc ctggagccca gaggagggca gcagaagggg  1719
gtggtgtctc caaccccca gcactgagga agaacggggc tcttctcatt tcacccctcc   1779
ctttctcccc tgccccagg actgggccac ttctgggtgg ggcagtgggt cccagattgg   1839
ctcacactga gaatgtaaga actacaaaca aaatttctat taaattaaat tttgtgtctc  1899
```

<210> SEQ ID NO 2
<211> LENGTH: 417
<212> TYPE: PRT
<213> ORGANISM: Homo sapiens

<400> SEQUENCE: 2

```
Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
                20                  25                  30

Trp Thr Ser Arg Trp Ile Glu Ser Lys His Lys Ser Asp Phe Gly Lys
            35                  40                  45

Phe Val Leu Ser Ser Gly Lys Phe Tyr Gly Asp Glu Glu Lys Asp Lys
        50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240
```

```
His Ile Pro Asp Pro Asp Ala Lys Lys Pro Glu Asp Trp Asp Glu Glu
            245                 250                 255

Met Asp Gly Glu Trp Glu Pro Pro Val Ile Gln Asn Pro Glu Tyr Lys
        260                 265                 270

Gly Glu Trp Lys Pro Arg Gln Ile Asp Asn Pro Asp Tyr Lys Gly Thr
    275                 280                 285

Trp Ile His Pro Glu Ile Asp Asn Pro Glu Tyr Ser Pro Asp Pro Ser
290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Glu Ala Glu Asp
    370                 375                 380

Lys Glu Asp Asp Glu Asp Lys Asp Glu Asp Glu Glu Asp Glu Glu Asp
385                 390                 395                 400

Lys Glu Glu Asp Glu Glu Glu Asp Val Pro Gly Gln Ala Lys Asp Glu
                405                 410                 415

Leu

<210> SEQ ID NO 3
<211> LENGTH: 24
<212> TYPE: DNA
<213> ORGANISM: Unknown
<220> FEATURE:
<223> OTHER INFORMATION: Primer

<400> SEQUENCE: 3
ggggaattca tggagataca ccta                                           24

<210> SEQ ID NO 4
<211> LENGTH: 23
<212> TYPE: DNA
<213> ORGANISM: Unknown
<220> FEATURE:
<223> OTHER INFORMATION: Primer

<400> SEQUENCE: 4
ggtggatcct tgagaacaga tgg                                            23

<210> SEQ ID NO 5
<211> LENGTH: 98
<212> TYPE: PRT
<213> ORGANISM: Human papillomavirus

<400> SEQUENCE: 5

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60
```

-continued

```
Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro

<210> SEQ ID NO 6
<211> LENGTH: 30
<212> TYPE: DNA
<213> ORGANISM: Unknown
<220> FEATURE:
<223> OTHER INFORMATION: Primer

<400> SEQUENCE: 6
ccggtctaga atgctgctcc ctgtgccgct                                           30

<210> SEQ ID NO 7
<211> LENGTH: 30
<212> TYPE: DNA
<213> ORGANISM: Unknown
<220> FEATURE:
<223> OTHER INFORMATION: Primer

<400> SEQUENCE: 7
ccggagatct cagctcgtcc ttggcctggc                                           30
```

US 7,342,002 B2

MOLECULAR VACCINE LINKING AN ENDOPLASMIC CHAPERONE POLYPEPTIDE TO AN ANTIGEN

This application is a U.S. National Phase Application file under 35, U.S.C. § 371 based on PCT/US01/24134, filed 2 Aug. 2001, which claimed priority from U.S. Provisional Application Ser. No. 60/222,902, filed 3 Aug. 2000.

STATEMENT AS TO FEDERALLY SPONSORED RESEARCH

This invention was made with Federal Government support under grants from National Institutes of Health; RO1 CA72631; from the NCDDG, RFA CA-95-020. The United States government may have certain rights in the invention.

BACKGROUND OF THE INVENTION

1. Field of the Invention

This invention, in the field of immunology and medicine, provides compositions and methods for inducing enhanced antigen-specific immune responses, particularly those mediated by cytotoxic T lymphocytes (CTL), using chimeric or hybrid nucleic acid molecules that encode an endoplasmic reticulum chaperone polypeptide, e.g., calreticulin, and a polypeptide or peptide antigen. Naked DNA and self-replicating RNA replicon vaccines are provided.

2. Description of the Background Art

DNA vaccines have become an attractive approach for inducing antigen-specific immunotherapy. Forms of DNA vaccines include "naked" DNA, such as plasmid DNA (U.S. Pat. Nos. 5,580,859; 5,589,466; 5,703,055), viral DNA, and the like. Basically, a DNA molecule encoding a desired immunogenic protein or peptide is administered to an individual and the protein is generated in vivo. Use of "naked" DNA vaccines has the advantages of being safe because, e.g., the plasmid itself has low immunogenicity, it can be easily prepared with high purity and, compared to proteins or other biological reagents, it is highly stable. However, DNA vaccines have limited potency. Several strategies have been applied to increase the potency of DNA vaccines, including, e.g., targeting antigens for rapid intracellular degradation; directing antigens to antigen presenting cells (APCs) by fusion to ligands for APC receptors; fusing antigens to chemokines or to antigenic pathogenic sequences, co-injection with cytokines or co-stimulatory molecules or adjuvant compositions.

Cancer vaccines are an attractive approach for cancer treatment because they may have the potency to eradicate systemic tumor in multiple sites in the body and the specificity to discriminate between neoplastic and non-neoplastic cells (Pardoll (1998) Nature Med. 4:525-531). Anti-tumor effects of the immune system are mainly mediated by cellular immunity. The cell-mediated component of the immune system is equipped with multiple effector mechanisms capable of eradicating tumors, and most of these anti-tumor immune responses are regulated by T cells. Therefore, it is hoped that cancer vaccines, particularly as DNA vaccines, aimed at enhancing tumor-specific T cell responses will be developed to control tumors.

HPV oncogenic proteins, E6 and E7, are co-expressed in most cervical cancers associated with HPV and are important in the induction and maintenance of cellular transformation. Therefore, vaccines targeting E6 or E7 proteins may provide an opportunity to prevent and treat HPV-associated cervical malignancies. HPV-16 E7, a well-characterized cytoplasmic/nuclear protein that is more conserved than E6 in HPV-associated cancer cells, has been exploited in a number of HPV vaccines.

Calreticulin (CRT), an abundant 46 kilodalton (kDa) protein located in the lumen of the cell's endoplasmic reticulum (ER), displays lectin activity and participates in the folding and assembly of nascent glycoproteins. See, e.g., Nash (1994) Mol. Cell. Biochem. 135:71-78; Hebert (1997) J. Cell Biol. 139:613-623; Vassilakos (1998) Biochemistry 37:3480-3490; Spiro (1996) J. Biol. Chem. 271:11588-11594. CRT associates with peptides transported into the ER by transporters that are associated with antigen processing, such as TAP-1 and TAP-2 (Spee (1997) Eur. J. Immunol. 27:2441-2449). CRT also forms complexes with peptides in vitro. Upon adminsitration to mice, these complexes, elicited peptide-specific CD8+ T cell responses (Basu (1999) J. Exp. Med. 189:797-802; Nair (1999) J. Immunol. 162:6426-6432). CRT purified from murine tumors elicited immunity specific for the tumor from which the CRT was taken, but not for an antigenically distinct tumor (Basu, supra). By pulsing mouse dendritic cells (DCs) in vitro with a CRT-peptide complex, the peptide was re-presented by MHC class I molecules on the DCs to stimulate a peptide-specific CTL response (Nair, supra).

CRT also has anti-angiogenic effects. CRT and a fragment comprising amino acid residues 1-180, which has been called "vasostatin," are endothelial cell inhibitors that can suppress tumor growth (Pike (1999) Blood. 94:2461-2468). Tumor growth and metastasis depend on the existence of an adequate blood supply. As tumors grow larger, adequate blood supply to the tumor tissue is often ensured by new vessel formation, a process termed angiogenesis. (Folkman (1982) Ann. NY Acad. Sci. 401:212-27; Hanahan (1996) Cell. 86:353-364). Therapeutic agents that target and damage tumor vasculature can prevent or delay tumor growth and even promote regression or dormancy.

Self-replicating RNA vaccines (RNA replicons) have emerged as an important, more potent form of nucleic acid vaccines. RNA replicon vaccines may be derived from alphavirus vectors, such as Sindbis virus (Xiong (1989) Science 243:1188-1191), Semliki Forest virus (Ying (1999) Nature Med. 5:823-827), or Venezuelan equine encephalitis virus (Pushko (1997) Virology 239:389-401) vectors. These vaccines are self-replicating and self-limiting and may be administered as either RNA or DNA, which is then transcribed into RNA replicons in transfected cells or in vivo. (Berglund (1998) Nature Biotechnol. 16:562-565). Self-replicating RNA infects a diverse range of cell types and allows the expression of the antigen of interest at high levels (Huang (1996) Curr. Opin. Biotechnol. 7:531-535). Additionally, self-replicating RNA eventually causes lysis of transfected cells because viral replication is toxic to infected host cells (Frolov (1996) J. Virol. 70:1182-1190). These vectors therefore do not raise the concern associated with naked DNA vaccines of integration into the host genome. This is particularly important for vaccine development targeting proteins that are potentially oncogenic, such as the HPV E6 and E7 proteins.

Chen (2000) Cancer Research 60:1035-1042 demonstrated that linkage of human papillomavirus type 16 (HPV-16) E7 antigen to *Mycobacterium tuberculosis* heat shock protein 70 (HSP70) leads to the enhancement of DNA vaccine potency. Other studies have demonstrated that immunization with heat shock protein (HSP) complexes isolated from tumor or virus-infected cells are able to induce potent anti-tumor (Janetzki (1998) J. Immunother. 21:269-276) or antiviral immunity (Heikema (1997) Immunol. Lett.

57:69-74). Immunogenic HSP-peptide complexes can also be reconstituted in vitro by mixing the peptides with HSPs (Ciupitu (1998) J. Exp. Med. 187:685-691). HSP-based protein vaccines can also be administered by fusing antigens to HSPs (Suzue (1996) J. Immunol. 156:873-879, HSP70 fusion protein elicited humoral and cellular immune responses to HIV-1 p24). These experiments demonstrate that 1) HSP-peptide complexes derived from tumor cells or virus-infected cells can stimulate tumor or virus-specific immunity; 2) the specificity of this immune response is caused by tumor-derived peptides that are bound to HSPs and not caused by the HSPs themselves; and 3) the immune response can be induced in mice with MHC either identical or different to the MHC of donor HSPs (Przepiorkha (1998) Mol. Med. Today 4:478-484; Srivastava (1998) Immunity 8:657-665). While these investigations have made HSPs more attractive for use in immunotherapy, the only HSP vaccines that have been tested thus far are in the form of protein-based vaccines or DNA-based vaccines.

SUMMARY OF THE INVENTION

The invention provides a nucleic acid encoding a chimeric protein comprising a first polypeptide domain comprising an endoplasmic reticulum chaperone polypeptide and a second polypeptide domain comprising at least one antigenic peptide. The antigenic peptide can comprise an MHC Class I-binding peptide epitope. The antigenic peptide, e.g., the MHC class I-binding peptide epitope, can be between about 8 amino acid residues and about 11 amino acid residues in length.

The endoplasmic reticulum chaperone polypeptide includes any ER polypeptide having chaperone functions similar to the exemplary chaperones calreticulin, calnexin, tapasin, or ER60 polypeptides; or, analogues or mimetics thereof, or, functional fragments thereof. Such functional fragments can be screened using routine screening tests, e.g., as described in Examples 1 and 2, below. Thus, in alternative embodiments, the endoplasmic reticulum chaperone polypeptide comprises or consists of a calnexin polypeptide or an equivalent thereof, an ER60 polypeptide or an equivalent thereof, a GRP94/GRP96 or a GRP94 polypeptide or an equivalent thereof, or, a tapasin polypeptide or an equivalent thereof.

In one embodiment, the calreticulin polypeptide comprises a human calreticulin polypeptide. In alternative embodiments, the human calreticulin polypeptide sequence can comprises SEQ ID NO:1, or, it can consist essentially of a sequence from about residue 1 to about residue 180 of SEQ ID NO:2, or, it can consist essentially of a sequence from about residue 181 to about residue 417 of SEQ ID NO:2.

In one embodiment, the antigen (e.g., the MHC class I-binding peptide epitope) is derived from a pathogen, e.g., it comprises a peptide expressed by a pathogen. The pathogen can be a virus, such as, e.g., a papilloma virus, a herpesvirus, a retrovirus (e.g., an immunodeficiency virus, such as HIV-1), an adenovirus, and the like. The papilloma virus can be a human papilloma virus; for example, the antigen (e.g., the Class I-binding peptide) can be derived from an HPV-16E7 polypeptide. In one embodiment, the HPV-16 E7 polypeptide is substantially non-oncogenic, i.e., it does not bind retinoblastoma polypeptide (pRB) or binds pRB with such low affinity that the HPV-16 E7 polypeptide is effectively non-oncogenic when expressed or delivered in vivo.

In alternative embodiments, the pathogen is a bacteria, such as *Bordetella pertrssis*; *Ehrlichia chaffeensis*; *Staphylococcus aureus*; *Toxoplasma gondii*; *Legionella pneumophila*; *Brucella suis*; *Salmoizella enterica*; *Mycobacterium avium*; *Mycobacterium tuberculosis*; *Listeria monocytogenes*; *Chlamydia trachomatis*; *Chlamydia pneumoniae*; *Rickettsia rickettsi*; or, a fungi, such as, e.g., *Paracoccidioides brasiliensis*; or other pathogen, e.g., *Plasmodium falciparum*.

In another embodiment, the MHC class I-binding peptide epitope is derived from a tumor cell. The tumor cell-derived peptide epitope can comprise a tumor associated antigen, e.g., a tumor specific antigen, such as, e.g., a HER-2/neu antigen.

In one embodiment, the isolated or recombinant nucleic acid molecule is operatively linked to a promoter, such as, e.g., a constitutive, an inducible or a tissue-specific promoter. The promoter can be expressed in any cell, including cells of the immune system, including, e.g., antigen presenting cells (APCs), e.g., in a constitutive, an inducible or a tissue-specific manner.

In alternative embodiments, the APCs are dendritic cells, keratinocytes, astrocytes, monocytes, macrophages, B lymphocytes, a microglial cell, or activated endothelial cells, and the like.

The invention also provides an expression cassette comprising a nucleic acid sequence encoding a chimeric protein comprising a first polypeptide domain comprising an endoplasmic reticulum chaperone polypeptide and a second polypeptide domain comprising at least one antigenic peptide. In alternative embodiments, the first domain comprises a calreticulin polypeptide and the second domain comprises an MHC class I-binding peptide epitope. In alternative embodiments, the expression cassette comprises an expression vector, a recombinant virus (e.g., an adenovirus, a retrovirus), a plasmid. The expression cassette can comprise a self-replicating RNA replicon. The self-replicating RNA replicon can comprise a Sindbis virus self-replicating RNA vector, such as, e.g., a Sindbis virus self-replicating RNA vector SINrep5 (U.S. Pat. No. 5,217,879). As with all applicable embodiments of the invention, the ER chaperone polypeptide can include any ER polypeptide having chaperone functions similar to the exemplary chaperones calreticulin, 1, tapasin, or ER60 polypeptides; or, analogues or mimetics thereof, or, functional fragments thereof.

The invention also provides a particle comprising a nucleic acid encoding a chimeric protein comprising a first polypeptide domain comprising an endoplasmic reticulum chaperone polypeptide and a second polypeptide domain comprising at least one antigenic peptide. In one embodiment, the isolated particle comprising an expression cassette comprising a nucleic acid sequence encoding a fusion protein comprising at least two domains, wherein the first domain comprises a calreticulin polypeptide and the second domain comprises an MHC class I-binding peptide epitope. The isolated particle can comprise any material suitable for particle bombardment, such as, e.g., gold. The ER chaperone polypeptide can include any ER polypeptide having chaperone functions similar to the exemplary chaperones calreticulin, calnexin, tapasin, or ER60 polypeptides, as discussed herein.

The invention also provides a cell comprising a nucleic acid sequence encoding a chimeric protein comprising a first polypeptide domain comprising an endoplasmic reticulum chaperone polypeptide and a second polypeptide domain comprising at least one antigenic peptide. In one embodiment, the cell comprises an expression cassette comprising a nucleic acid sequence encoding a fusion protein comprising at least two domains, wherein the first domain comprises a calreticulin polypeptide and the second domain comprises an MHC class I-binding peptide epitope. The cell can be transfected, infected, transduced, etc., with a nucleic acid of the invention or infected with a recombinant virus of the invention. The cell can be isolated from a non-human transgenic animal comprising cells comprising expression cassettes of the invention. Any cell can comprise an expression cassette of the invention, such as, e.g., cells of the immune system or antigen presenting cells (APCs). The APCs can be a dendritic cell, a keratinocyte, a macrophage, a monocyte, a B lymphocyte, an astrocyte, a microglial cell, or an activated endothelial cell.

The invention also provides a chimeric polypeptide comprising a first polypeptide domain comprising an endoplasmic reticulum chaperone polypeptide and a second polypeptide domain comprising at least one antigenic peptide. The antigenic peptide can comprise an MHC Class I-binding peptide epitope. The ER chaperone polypeptide can be chemically linked to the antigenic peptide, e.g., as a fusion protein (e.g., a peptide bond), that can be, e.g., synthetic or recombinantly produced, in vivo or in vitro. The polypeptide domains can be linked by a flexible chemical linker.

In alternative embodiments, the first polypeptide domain of the chimeric polypeptide can be closer to the amino terminus than the second polyeptide domain, or, the second polypeptide domain can be closer to the amino terminus than the first polypeptide domain. The ER chaperone polypeptide can include any ER polypeptide having chaperone functions similar to the exemplary chaperones calreticulin, calnexin, tapasin, or ER60 polypeptides, as discussed herein.

The invention provides a pharmaceutical composition comprising a composition of the invention capable of inducing or enhancing an antigen specific immune response and a pharmaceutically acceptable excipient. In alternative embodiments, the composition comprises: a chimeric polypeptide comprising a first domain comprising an endoplasmic reticulum chaperone polypeptide and a second domain comprising an antigenic peptide; a nucleic acid molecule encoding a fusion protein comprising a first polypeptide domain comprising an endoplasmic reticulum chaperone polypeptide and a second polypeptide domain an antigenic peptide; an expression cassette comprising a nucleic acid sequence encoding a fusion protein comprising a first domain comprising an endoplasmic reticulum chaperone polypeptide and a second domain comprising an antigenic peptide; a particle comprising a nucleic acid sequence encoding a fusion protein comprising a first domain comprising an endoplasmic reticulum chaperone polypeptide and a second domain comprising an antigenic peptide; or, a cell comprising a nucleic acid sequence encoding a fusion protein comprising a first domain comprising an endoplasmic reticulum chaperone polypeptide coding sequence and a second domain comprising an antigenic peptide. The ER chaperone polypeptide can include any ER polypeptide having chaperone functions similar to the exemplary chaperones calreticulin, calnexin, tapasin, or ER60 polypeptides, as discussed herein.

The invention provides a method of inducing or enhancing an antigen specific immune response comprising: (a) providing a composition comprising a composition of the invention capable of inducing or enhancing an antigen specific immune response, which, in alternative embodiments, can be: a chimeric polypeptide comprising a first domain comprising an endoplasmic reticulum chaperone polypeptide and a second domain comprising an antigenic peptide; a nucleic acid molecule encoding a fusion protein comprising a first polypeptide domain comprising an endoplasmic reticulum chaperone polypeptide and a second polypeptide domain an antigenic peptide; an expression cassette comprising a nucleic acid sequence encoding a fusion protein comprising a first domain comprising an endoplasmic reticulum chaperone polypeptide and a second domain comprising an antigenic peptide; a particle comprising a nucleic acid sequence encoding a fusion protein comprising a first domain comprising an endoplasmic reticulum chaperone polypeptide and a second domain comprising an antigenic peptide; or, a cell comprising a nucleic acid sequence encoding a fusion protein comprising a first domain comprising an endoplasmic reticulum chaperone polypeptide coding sequence and a second domain comprising an antigenic peptide; and, (b) administering an amount of the composition sufficient to induce or enhance an antigen specific immune response. The antigen specific immune response can comprise cellular response, such as a $CD8^+$ CTL response. The antigen specific immune response can also comprise an antibody-mediated response, or, a humoral and a cellular response.

In practicing the method the composition can administered ex vivo, or, the composition can be administered ex vivo to an antigen presenting cell (APC). In alternative embodiments, the APC is a dendritic cell, a keratinocyte, a macrophage, a monocyte, a B lymphocyte, an astrocyte, a microglial cell, or an activated endothelial cell. The APC can be a human cell. The APC can be isolated from an in vivo or in vitro source. The method can further comprise administering the ex vivo-treated APC to a mammal, a human, a histocompatible individual, or to the same individual from which it was isolated. Alternatively, the composition is administered directly in vivo to a mammal, e.g., a human.

The composition can be administered intramuscularly, intradermally, or subcutaneously. The composition, e.g., the nucleic acid, expression cassette or particle, can be administered by ballistic injection. The composition can be administered intratumorally or peritumorally.

In alternative embodiment of the method, the antigenic peptide can be derived from a virus, such as a human papilloma virus. The antigenic peptide can be an HPV-16 E7 peptide. The antigenic peptide can be a tumor-specific or a tumor-associated peptide, such as a HER-2/neu peptide.

The invention provides a method of increasing the numbers of $CD8^+$ CTLs specific for a desired antigen in an individual comprising: (a) providing a composition comprising: a chimeric polypeptide comprising a first domain comprising an endoplasmic reticulum chaperone polypeptide and a second domain comprising an antigenic peptide; a nucleic acid molecule encoding a fusion protein comprising a first polypeptide domain comprising an endoplasmic reticulum chaperone polypeptide and a second polypeptide domain an antigenic peptide; an expression cassette comprising a nucleic acid sequence encoding a fusion protein comprising a first domain comprising an endoplasmic reticulum chaperone polypeptide and a second domain comprising an antigenic peptide; a particle comprising a nucleic acid sequence encoding a fusion protein comprising a first domain comprising an endoplasmic reticulum chaperone polypeptide and a second domain comprising an antigenic peptide; or, a cell comprising a nucleic acid sequence encoding a fusion protein comprising a first domain comprising an endoplasmic reticulum chaperone polypeptide coding sequence and a second domain comprising an antigenic peptide; wherein the MIC class I-binding peptide epitope is derived from the antigen, and, (b) administering an amount of the composition sufficient to increase the numbers of antigen-specific $CD8^+$ CTL.

The invention provides a method of inhibiting the growth of a tumor in an individual comprising: (a) providing a composition comprising: a chimeric polypeptide comprising a first domain comprising an endoplasmic reticulum chaperone polypeptide and a second domain comprising an antigenic peptide; a nucleic acid molecule encoding a fusion protein comprising a first polypeptide domain comprising an endoplasmic reticulum chaperone polypeptide and a second polypeptide domain an antigenic peptide; an expression cassette comprising a nucleic acid sequence encoding a fusion protein comprising a first domain comprising an endoplasmic reticulum chaperone polypeptide and a second domain comprising an antigenic peptide; a particle comprising a nucleic acid sequence encoding a fusion protein comprising a first domain comprising an endoplasmic reticulum chaperone polypeptide and a second domain comprising an antigenic peptide; or, a cell comprising a nucleic acid sequence encoding a fusion protein comprising a first domain comprising an endoplasmic reticulum chaperone polypeptide coding sequence and a second domain comprising an antigenic peptide; and, (b) administering an amount of the composition sufficient to inhibit the growth of the tumor. In one embodiment of the invention, the composition is administered intratumorally or peritumorally. The composition can be co-administered with a second composition comprising anti-angiogenesis activity, such as angiostatin, endostatin or TIMP-2, or an equivalent thereof, or a mixture thereof. The composition can be co-administered with a radiotherapy or a chemotherapy composition.

The invention also provides self-replicating RNA virus constructs comprising nucleic acids encoding the immune response enhancing fusion proteins of the invention, including, e.g., chimeric proteins comprising ER chaperones and antigenic peptides, heat shock proteins and antigenic peptides, and equivalents thereof and mixtures thereof. In one embodiment, the self-replicating RNA virus comprises a Sindbis virus self-replicating RNA vector, such as SINrep5, as discussed in Example 2, below.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

FIG. 2 shows the two-dimensional histograms summarizing FACS (flow cytometry) analysis of splenocytes from mice vaccinated with negative control and DNA expressing CRT alone, E7 alone and the CRT/E7 fusion protein of the invention, and stained with antibodies for CD8 and INF-gamma; as discussed in Example 1, below. FIG. 2B shows a schematic summary of the histogram data.

FIG. 9 shows a schematic diagram of SINrep5, SINrep5-HSP70, SINrep5-E7, SINrep5-E7/HSP70 DNA constructs. FIG. 9 shows a schematic diagram of RNA transcript derived from these DNA constructs using SP6 RNA polymerase as described in detail in Example 2, below.

DESCRIPTION OF THE PREFERRED EMBODIMENTS

Figure 1:
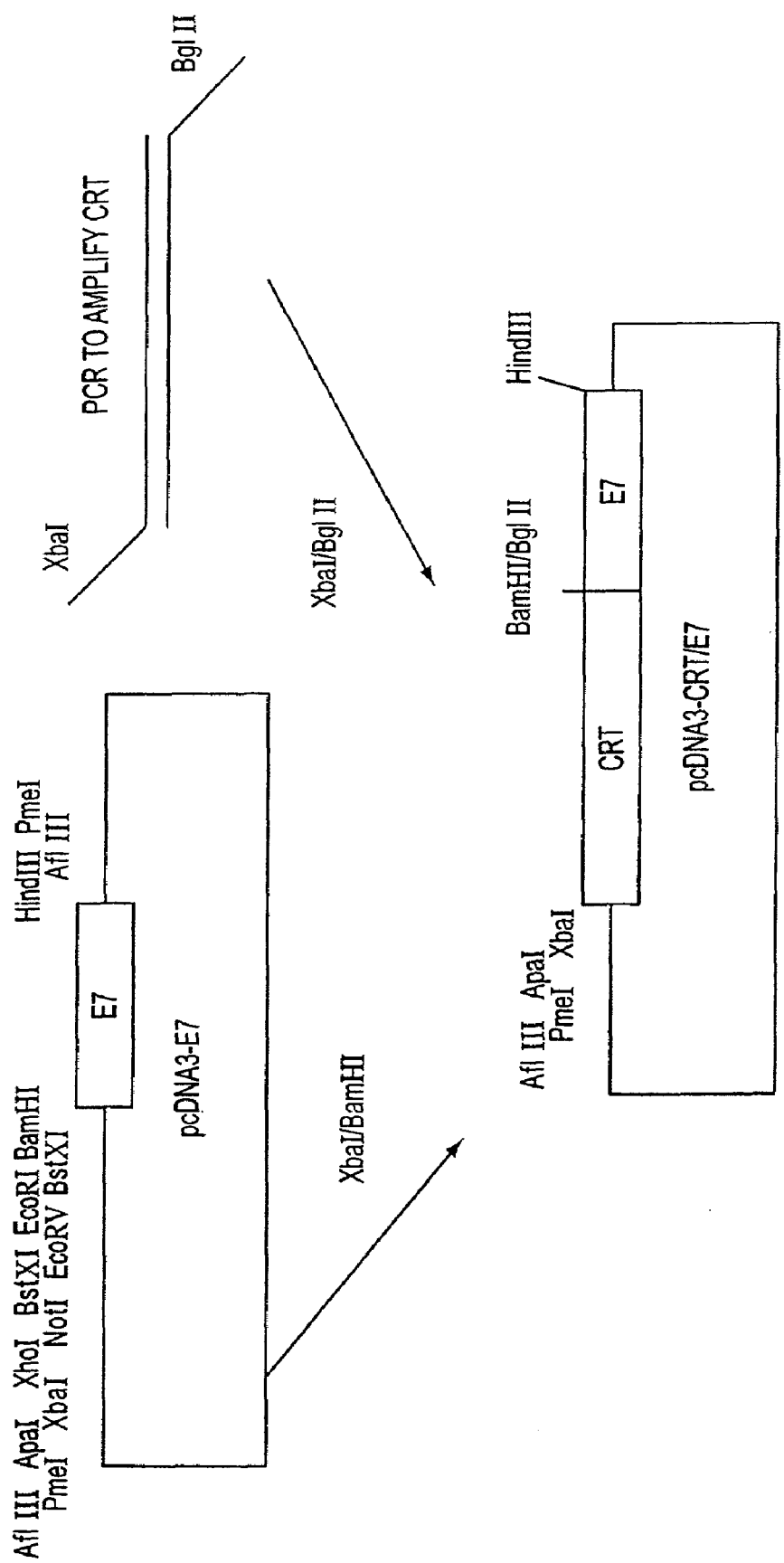
FIG. 1 shows a schematic diagram of the recombinant DNA constructs encoding calreticulin (CRT), HPV polypeptide E7, and the fusion protein of the invention calreticulin/E7 (CRT/E7), as discussed in Example 1, below.

The invention provides compositions and methods for enhancing the immune responses, particularly cytotoxic T cell immune responses, induced by ex vivo or in vivo administration of chimeric polypeptides comprising an endoplasmic reticulum chaperone polypeptide and at least one antigenic peptide. The chimeric polypeptides can be "indirectly" administered by administration of a nucleic acid that encodes the chimeric molecule; the nucleic acid construct, and thus the fusion protein, is expressed in vivo. In one embodiment, the chimeric nucleic acids or polypeptides are administered in the form of DNA vaccines.

The fusion protein comprises at least two domains: the first domain comprises a endoplasmic reticulum chaperone polypeptide and the second domain comprises an peptide derived from an antigen against which it is desired to induce an immune response. Any endoplasmic reticulum chaperone polypeptide, or functional fragment or variation thereof, can be used in the invention, such as calreticulin, tapasin, ER60 or calnexin polypeptides.

The second domain of the chimeric molecule comprises an antigenic peptide, which can be derived from a pathogen, a cancer, or any source to which induction, enhancement or suppression of an immune response is desired. In one embodiment, the peptide comprises an MHC class I-binding peptide epitope.

In the methods of the invention, the chimeric polypeptide or nucleic acid that encodes it are applied to induce or enhance immune responses. In one embodiment, the compositions of the invention synergistically enhance immune responses and antitumor effects through both immunological and anti-angiogenic mechanisms.

The experiments described herein demonstrate that the methods of the invention can enhance a cellular immune response, particularly, a CTL reactivity, induced by a DNA vaccine encoding an epitope of a human pathogen. Human HPV-16 E7 was used. It is a model antigen for vaccine development because human papillomaviruses (HPVs), particularly HPV-16, are associated with most human cervical cancers. The oncogenic HPV protein E7 is important in the induction and maintenance of cellular transformation and co-expressed in most HPV-containing cervical cancers and their precursor lesions. Therefore, cancer vaccines, such as the compositions of the invention, that target E7 can be used to control of HPV-associated neoplasms (Wu (1994) Curr. Opin. Immunol. 6:746-754).

As described in Example 1, below, the results of these experiments demonstrate that DNA vaccines comprising nucleic acid encoding a fusion protein comprising CRT linked to full-length E7 polypeptide can enhance the potency of DNA vaccines. DNA vaccines of the invention containing chimeric CRT/E7 fusion genes were administered to mice by ballistic subcutaneous methods. They induced increased E7-specific CD8+ CTL precursors, thereby improving immune protection against the tumors. This increase in E7-specific CD8+ T cell precursors was significant as compared to DNA vaccines containing wild-type E7 or CRT genes alone.

Furthermore, treatment of C57BL/6 mice (an inbred strain with a normal immune system) or nude mice (a strain lacking T cells and a functional immune system) with either CRT DNA or chimeric CRT/E7 DNA led to reduction of lung metastatic nodules and inhibition of angiogenesis within the lung nodules. Thus, the DNA vaccines of the invention encoding chimeric CRT/E7 represents a unique approach that combines immunological and anti-angiogenic approaches for the generation of potent anti-tumor effects.

As discussed above, while investigations have made heat shock proteins (HSPs) more attractive for use in immunotherapy, the only HSP vaccines that have been tested thus far are in the form of protein-based vaccines or DNA-based vaccines. This invention for the first time incorporates and describes the administration of antigens, such as HSPs and the chimeric polypeptides of the invention, in the form of self-replicating RNA vaccines.

As described in Example 2, below, expression of an HSP70-human papillomavirus type 16 (HPV-16) E7 fusion protein in a self-replicating RNA vaccine greatly enhanced the potency of this antigenic polypeptide when it was expressed in vivo. Results described below demonstrated that an RNA replicon vaccine containing E7/HSP70 fusion genes induced significantly higher E7-specific T cell-mediated immune responses than vaccines containing the wild type E7 gene in vaccinated mice. In vitro studies demonstrated that E7 antigen from E7/HSP70 RNA replicon-transfected apoptotic cells can be taken up by bone marrow-derived dendritic cells and presented more efficiently through the MHC class I pathway than wild-type E7 RNA replicon-transfected apoptotic cells. The fusion of HSP70 to E7 converted a less effective vaccine into one with significant potency against E7-expressing tumors. These results demonstrated that the use of self-replicating RNA vaccines can enhance the immunogenicity of the fusion proteins of the invention.

A potential mechanism for the enhanced antigen-specific $CD8^+$ T cell immune responses in vivo is the presentation of antigen through the MHC class I pathway by uptake of apoptotic bodies from cells expressing the antigen, also called "cross-priming". As discussed in Example 2, below, CTL assays demonstrated enhanced MHC class I presentation of HPV E7 polypeptide in bone marrow derived dendritic cells pulsed with apoptotic cells transfected by SIN-rep5-E7/HSP70 RNA.

Definitions

Unless defined otherwise, all technical and scientific terms used herein have the meaning commonly understood by a person skilled in the art to which this invention belongs. As used herein, the following terms have the meanings ascribed to them unless specified otherwise.

The term "anti-angiogenic activity" as used herein means any form of inhibition of blood vessel growth (e.g., capillary, arteriole, etc.); thus, such activity would include a slowing in the growth of blood vessels, or a substituent thereof, including, e.g., slowing or inhibiting the growth of endothelial cells.

The term "antigen" or "immunogen" as used herein refers to a compound or composition comprising a peptide, polypeptide or protein which is "antigenic" or "immunogenic" when administered (or expressed in vivo by an administered nucleic acid, e.g., a DNA vaccine) in an appropriate amount (an "immunogenically effective amount"), i.e., is capable of eliciting, augmenting or boosting a cellular and/or humoral immune response either alone or in combination or linked or fused to another substance (which can be administered at once or over several intervals).

"Calnexin" describes the well-characterized membrane protein of the endoplasmic reticulum (ER) that functions as a molecular chaperone and as a component of the ER quality control machinery. Calreticulin is a soluble analogue of calnexin in vivo, calreticulin and calnexin play important roles in quality control during protein synthesis, folding, and posttranslational modification. Calnexin polypeptides, and equivalents and analogues thereof, are species in the genus of ER chaperone polypeptides, as described herein (Wilson (2000) J. Biol. Chem. 275:21224-2132; Danilczyk (2000) J. Biol. Chem. 275:13089-13097; U.S. Pat. No. Nos. 6,071, 743 and 5,691,306).

"Calreticulin" or "CRT" describes the well-characterized ~46 kDa resident protein of the ER lumen that has lectin activity and participates in the folding and assembly of nascent glycoproteins. CRT acts as a "chaperone" polypeptide and a member of the MHC class I transporter TAP complex; CRT associates with TAP1 and TAP2 transporters, tapasin, MHC Class I heavy chain polypeptide and β2 microglobulin to function in the loading of peptide epitopes onto nascent MHC class I molecules (Jorgensen (2000) Eur. J. Biochem. 267:2945-2954). The term "calreticulin" or "CRT" refers to polypeptides and nucleic acids molecules having substantial identity (defined herein) to the exemplary CRT sequences as described herein. A CRT polypeptide is a polypeptides comprising a sequence identical to or substantially identical (defined herein) to the amino acid sequence of CRT. An exemplary nucleotide and amino acid sequence for a CRT used in the present compositions and methods are SEQ ID NO:1 and SEQ ID NO:2, respectively. The terms "calreticulin" or "CRT" encompass native proteins as well as recombinantly produced modified proteins that induce an immune response, including a CTL response. The terms "calreticulin" or "CRT" encompass homologues and allelic variants of CRT, including variants of native proteins constructed by in vitro techniques, and proteins isolated from natural sources. The CRT polypeptides of the invention, and sequences encoding them, also include fusion proteins comprising non-CRT sequences, particularly MHC class I-binding peptides; and also further comprising other domains, e.g., epitope tags, enzyme cleavage recognition sequences, signal sequences, secretion signals and the like.

The term "endoplasmic reticulum chaperone polypeptide" as used herein means any polypeptide having substantially the same ER chaperone function as the exemplary chaperone proteins CRT, tapasin, ER60 or calnexin. Thus, the term includes all functional fragments or variants or mimics thereof. A polypeptide or peptide can be routinely screened for its activity as an ER chaperone using assays known in the art, such as that set forth in Example 1. While the invention is not limited by any particular mechanism of action, in vivo chaperones promote the correct folding and oligomerization of many glycoproteins in the ER, including the assembly of the MHC class I heterotrimeric molecule (heavy (H) chain, β2m, and peptide). They also retain incompletely assembled MHC class I heterotrimeric complexes in the ER (Hauri (2000) FEBS Lett. 476:32-37).

The term "epitope" as used herein refers to an antigenic determinant or antigenic site that interacts with an antibody or a T cell receptor (TCR), e.g., the MHC class I-binding peptide compositions used in the methods of the invention. An "antigen" is a molecule or chemical structure that either induces an immune response or is specifically recognized or bound by the product of an immune response, such as an antibody or a CTL. The specific conformational or stereochemical "domain" to which an antibody or a TCR bind is an "antigenic determinant" or "epitope." TCRs bind to peptide epitopes which are physically associated with a third molecule, a major histocompatibility complex (MHC) class I or class II protein.

The terms "ER60" or "GRP94" or "gp96" or "glucose regulated protein 94" as used herein describes the well-characterized ER chaperone polypeptide that is the ER representative of the heat shock protein-90 (HSP90) family of stress-induced proteins. These bind to a limited number of proteins in the secretory pathway, possibly by recognizing advanced folding intermediates or incompletely assembled proteins. ER60 polypeptides, and equivalents and analogues thereof, are species in the genus of ER chaperone polypeptides, as described herein (Argon (1999) Semin. Cell Dev. Biol. 10:495-505; Sastry (1999) J. Biol. Chem. 274:12023-12035; Nicchitta (1998) Curr. Opin. Immunol. 10:103-109; U.S. Pat. No. 5,981,706).

The term "expression cassette" or "expression vector" as used herein refers to a nucleotide sequence which is capable of affecting expression of a protein coding sequence in a host compatible with such sequences. Expression cassettes include at least a promoter operably linked with the polypeptide coding sequence; and, optionally, with other sequences, e.g., transcription termination signals. Additional factors necessary or helpful in effecting expression may also be included, e.g., enhancers. "Operably linked" refers to linkage of a promoter upstream from a DNA sequence such that the promoter mediates transcription of the DNA sequence. Thus, expression cassettes include plasmids, recombinant viruses, any form of a recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons (see Example 2, below), bacteriophages) to which fragments of DNA may be attached and become replicated. Vectors thus include, but are not limited to RNA, autonomous self-replicating circular or linear DNA or RNA, e.g., plasmids, viruses, and the like (U.S. Pat. No. 5,217,879), and includes both the expression and nonexpression plasmids. Where a recombinant microorganism or cell culture is described as hosting an "expression vector" this includes both extrachromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The term "chemically linked" refers to any chemical bonding of two moieties, e.g., as in one embodiment of the invention, where an ER chaperone polypeptide is chemically linked to an antigenic peptide. Such chemical linking includes the peptide bonds of a recombinantly or in vivo generated fusion protein.

The term "chimeric" or "fusion" polypeptide or protein refers to a composition comprising at least one polypeptide or peptide sequence or domain which is associated with a second polypeptide or peptide domain. One embodiment of this invention is an isolated or recombinant nucleic acid molecule encoding a fusion protein comprising at least two domains, wherein the first domain comprises an endoplasmic reticulum chaperone, e.g., CRT, and the second domain comprising an antigenic epitope, e.g., an MHC class I-binding peptide epitope. Additional domains can comprise a polypeptide, peptide, polysaccharide, or the like. The "fusion" can be an association generated by a peptide bond, a chemical linking, a charge interaction (e.g., eletrostatic attractions, such as salt bridges, H-bonding, etc.) or the like. If the polypeptides are recombinant, the "fusion protein" can be translated from a common message. Alternatively, the compositions of the domains can be linked by any chemical or electrostatic means. The chimeric molecules of the invention (e.g., CRT-class I-binding peptide fusion proteins) can also include additional sequences, e.g., linkers, epitope tags, enzyme cleavage recognition sequences, signal sequences, secretion signals, and the like. Alternatively, a peptide can be linked to a carrier simply to facilitate manipulation or identification/location of the peptide.

The term "immunogen" or "immunogenic composition" refers to a compound or composition comprising a peptide, polypeptide or protein which is "immunogenic," i.e., capable of eliciting, augmenting or boosting a cellular and/or humoral immune response, either alone or in combination or linked or fused to another substance. An immunogenic composition can be a peptide of at least about 5 amino acids, a peptide of 10 amino acids in length, a fragment 15 amino acids in length, a fragment 20 amino acids in length or greater; smaller immunogens may require presence of a "carrier" polypeptide e.g., as a fusion protein, aggregate, conjugate or mixture, preferably linked (chemically or otherwise) to the immunogen. The immunogen can be recombinantly expressed from a vaccine vector, which can be naked DNA comprising the immunogen's coding sequence operably linked to a promoter, e.g., an expression cassette. The immunogen includes one or more antigenic determinants or epitopes which may vary in size from about 3 to about 15 amino acids.

The term "isolated" as used herein, when referring to a molecule or composition, such as, e.g., a CRT nucleic acid or polypeptide, means that the molecule or composition is separated from at least one other compound, such as a protein, other nucleic acids (e.g., RNAs), or other contaminants with which it is associated in vivo or in its natural state. Thus, a CRT composition is considered isolated when it has been isolated from any other component with which it is natively associated, e.g., cell membrane, as in a cell extract. An isolated composition can, however, also be substantially pure. An isolated composition can be in a homogeneous state and can be dry or in an aqueous solution. Purity and homogeneity can be determined, for example, using analytical chemistry techniques such as polyacrylamide gel electrophoresis (SDS-PAGE) or high performance liquid chromatography (HPLC). Thus, the isolated compositions of this invention do not contain materials normally associated with their in situ environment. Even where a protein has been isolated homogenous or dominant band, there are trace contaminants which co-purify with the desired protein.

The phrase "the HPV-16 E7 polypeptide is non-oncogenic" as used herein means a variant (e.g., deletion, substitution, and the like) of the HPV-16 E7 polypeptide that does not 3 bind retinoblastoma polypeptide ORB) or binds pRB with such low affinity that the HPV-16 E7 polypeptide variant is substantially non-oncogenic. T2V polypeptides, including HPV-16 E7 polypeptide, are well described in the art; for HPV-16 E7 GenBank Accession No. AF125673 (Jun. 1, 1999) shows the complete HPV-16 genome and the HPV-16 E7 protein, having the sequence SEQ ED NO:5 (see below).

The terms "polypeptide," "protein," and "peptide" include compositions of the invention that also include "analogues," or "conservative variants" and "mimetics" or "peptidomimetics" with structures and activity that substantially correspond to the polypeptide from which the variant was derived, including, e.g., human CRT or the Class I-binding peptide epitope, as the HPV-16 E7 polypeptide, as discussed in detail, below.

The term "pharmaceutical composition" refers to a composition suitable for pharmaceutical use, e.g., as a vaccine, in a subject. The pharmaceutical compositions of this invention are formulations that comprise a pharmacologically effective amount of a composition comprising, e.g., a nucleic acid, or vector, or cell of the invention, and a pharmaceutically acceptable carrier.

The term "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "recombinant" refers to (1) a polynucleotide synthesized or otherwise manipulated in vitro (e.g., "recombinant polynucleotide"), (2) methods of using recombinant polynucleotides to produce gene products in cells or other biological systems, or (3) a polypeptide ("recombinant protein") encoded by a recombinant polynucleotide. For example, recombinant CRT or an MHC class I-binding peptide epitope can be recombinant as used to practice this invention. "Recombinant means" also encompass the ligation of nucleic acids having various coding regions or domains or promoter sequences from different sources into an expression cassette or vector for expression of, e.g., inducible or constitutive expression of polypeptide coding sequences in the vectors used to practice this invention.

The term "self-replicating RNA replicon" refers to constructs based on RNA viruses, e.g., alphavirus genome RNAs (e.g., Sindbis virus, Semliki Forest virus, etc.), that have been engineered to allow expression of heterologous RNAs and proteins. These recombinant vectors are self-replicating (i.e., they are "replicons") and can be introduced into cells as naked RNA or DNA, as described in detail, below. In one embodiment, the self-replicating RNA replicon comprises a Sindbis virus self-replicating RNA vector SINrep5, which is described in detail in U.S. Pat. No. 5,217,879.

The term "systemic administration" refers to administration of a composition or agent such as the molecular vaccine or the CRT-Class I-binding peptide epitope fusion protein described herein, in a manner that results in the introduction of the composition into the subject's circulatory system. The term "regional" administration refers to administration of a composition into a specific anatomical space, such as intraperitoneal, intrathecal, subdural, or to a specific organ, and the like. For example, regional administration includes administration of the composition or drug into the hepatic artery. The term "local administration" refers to administration of a composition or drug into a limited, or circumscribed, anatomic space, such as intratumoral injection into a tumor mass, subcutaneous injections, intramuscular injections, and the like. Any one of skill in the art would understand that local administration or regional administration may also result in entry of the composition or drug into the circulatory system.

"Tapasin" is the known ER chaperone polypeptide, as discussed above. While not limited by any particular mechanism of action, in vivo, tapasin is a subunit of the TAP (transporter associated with antigen processing) complex and binds both to TAP1 and MHC class I polypeptides. Tapasin polypeptides, and equivalents and analogues thereof, are species in the genus of ER chaperone polypeptides, as described herein (Barnden (2000) J. Immunol. 165:322-330, Li(2000) *J. Biol. Chem.* 275:1581-1586).

Generating and Manipulating of Nucleic Acids

The methods of the invention provide for the administration of nucleic acids encoding a CRT-Class I epitope binding peptide fusion protein, as described above. Recombinant CRT-containing fusion proteins can be synthesized in vitro or in vivo. Nucleic acids encoding these compositions can be in the form of "naked DNA" or they can be incorporated in plasmids, vectors, recombinant viruses (e.g., "replicons") and the like for in vivo or ex vivo administration. Nucleic acids and vectors of the invention can be made and expressed in vitro or in vivo, a variety of means of making and expressing these genes and vectors can be used. One of skill will recognize that desired gene activity can be obtained by modulating the expression or activity of the genes and nucleic acids (e.g., promoters) within vectors used to practice the invention. Any of the known methods described for increasing or decreasing expression or activity, or tissue specificity, of genes can be used for this invention. The invention can be practiced in conjunction with any method or protocol known in the art, which are well described in the scientific and patent literature.

General Techniques

The nucleic acid sequences used to practice this invention, whether RNA, cDNA, genomic DNA, vectors, recombinant viruses or hybrids thereof, may be isolated from a variety of sources, genetically engineered, amplified, and/or expressed recombinantly. Any recombinant expression system can be used, including, in addition to bacterial cells, e.g., mammalian, yeast, insect or plant cell expression systems.

Alternatively, these nucleic acids can be synthesized in vitro by well-known chemical synthesis techniques, as described in, e.g., Carruthers (1982) Cold Spring Harbor Symp. Quant. Biol. 47:411-418; Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with an appropriate primer sequence.

The sequences of CRT, including human CRT, are well known in the art (McCauliffe (1990) J. Clin. Invest. 86:332-335; Burns (1994) Nature 367:476-480; Coppolino (1998) Int. J. Biochem. Cell Biol. 30:553-558). The nucleic acid sequence appears as GenBank Accession

```
No. NM 004343 and is SEQ ID NO: 1.

1 gtccgtactg cagagccgct gccggagggt cgttttaaag ggccgcgttg ccgcccctc
  61 ggcccgccat gctgctatcc gtgccgctgc tgctcggcct cctcggcctg gccgtcgccg
 121 agcccgccgt ctacttcaag gagcagtttc tggacggaga cgggtggact tcccgctgga
 181 tcgaatccaa acacaagtca gattttggca aattcgttct cagttccggc aagttctacg
 241 gtgacgagga gaaagataaa ggtttgcaga caagccagga tgcacgcttt tatgctctgt
 301 cggccagttt cgagcctttc agcaacaaag gccagacgct ggtggtgcag ttcacggtga
 361 aacatgagca gaacatcgac tgtggggcg gctatgtgaa gctgtttcct aatagtttgg
 421 accagacaga catgcacgga gactcagaat acaacatcat gtttggtccc gacatctgtg
 481 gccctggcac caagaaggtt catgtcatct tcaactacaa gggcaagaac gtgctgatca
 541 acaaggacat ccgttgcaag gatgatgagt ttacacacct gtacacactg attgtgcggc
 601 cagacaacac ctatgaggtg aagattgaca cagccaggt ggagtccggc tccttggaag
 661 acgattggga cttcctgcca cccaagaaga taaaggatcc tgatgcttca aaaccggaag
 721 actgggatga gcgggccaag atcgatgatc ccacagactc caagcctgag gactgggaca
 781 agcccgagca tatccctgac cctgatgcta agaagcccga ggactgggat gaagagatgg
 841 acggagagtg ggaaccccca gtgattcaga ccctgagta caagggtgag tggaagcccc
 901 ggcagatcga caacccagat tacaagggca cttggatcca cccagaaatt gacaacccg
 961 agtattctcc cgatcccagt atctatgcct atgataactt tggcgtgctg ggcctggacc
1021 tctggcaggt caagtctggc accatctttg acaacttcct catcaccaac gatgaggcat
1081 acgctgagga gtttggcaac gagacgtggg gcgtaacaaa ggcagcagag aaacaaatga
1141 aggacaaaca ggacgaggag cagaggctta aggaggagga agaagacaag aaacgcaaag
1201 aggaggagga ggcagaggac aaggaggatg atgaggacaa agatgaggat gaggaggatg
1261 aggaggacaa ggaggaagat gaggaggaag atgtccccgg ccaggccaag gacgagctgt
1321 agagaggcct gcctccaggg ctggactgag gcctgagcgc tcctgccgca gagcttgccg
1381 cgccaaataa tgtctctgtg agactcgaga actttcattt ttttccaggc tggttcggat
1441 ttggggtgga ttttggtttt gttcccctcc tccactctcc cccacccct cccgcccctt
1501 tttttttttt ttttaaact ggtattttat cctttgattc tccttcagcc ctcacccctg
```

```
-continued 1561 gttctcatct ttcttgatca acatcttttc ttgcctctgt gccccttctc tcatctctta 1621 gctccctcc aacctggggg gcagtggtgt ggagaagcca caggcctgag atttcatctg 1681 ctctccttcc tggagcccag aggagggcag cagaaggggg tggtgtctcc aaccccccag 1741 cactgaggaa gaacggggct cttctcattt caccccctccc tttctcccct gccccagga 1801 ctgggccact tctgggtggg gcagtgggtc ccagattggc tcacactgag aatgtaagaa 1861 ctacaaacaa aatttctatt aaattaaatt ttgtgtctc                1899
```

Techniques for the manipulation of nucleic acids, such as, e.g., generating mutations in sequences, subcloning, labeling probes, sequencing, hybridization and the like are well described in the scientific and patent literature. See, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immunoelectrophoresis, (radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCP, other nucleic acid or target or signal amplification methods, radiolabeling, scintillation counting, and affinity chromatography.

Amplification of Nucleic Acids

Oligonucleotide primers can be used to amplify nucleic acids to generate fusion protein coding sequences used to practice the invention, to monitor levels of vaccine after ill vivo administration (e.g., levels of a plasmid or virus), to confirm the presence and phenotype of activated CTLs, and the like. The skilled artisan can select and design suitable oligonucleotide amplification primers using known sequences, e.g., SEQ ID NO:1. Amplification methods are also well known in the art, and include, e.g., polymerase chain reaction, PCR(*PCR Protocols, A Guide to Methods and Applications*, ed. Innis, Academic Press, N.Y. (1990) and *PCR Strategies* (1995), ed. Innis, Academic Press, Inc., N.Y., ligase chain reaction (LCR) (Wu (1989) Genomics 4:560; Landegren (1988) Science 241:1077; Barringer (1990) Gene S9:117); transcription amplification (Kwoh (1989) Proc. Natl. Acad. Sci. USA 86:1173); and, self-sustained sequence replication (Guatelli (1990) Proc. Natl. Acad. Sci. USA 87:1874); Qβ replicase amplification (Smith (1997) J. Clin. Microbiol. 35:1477-1491; Burg (1996) Mol. Cell. Probes 10:257-271) and other RNA polymerase mediated techniques (NASBA, Cangene, Mississauga, Ontario; Berger (1987) Methods Enzymol. 152:307-316; U.S. Pat. Nos. 4,683,195 and 4,683,202; Sooknanan (1995) Biotechnology 13:563-564).

Cloning and Construction of Expression Cassettes

Expression cassettes, including plasmids, recombinant viruses (e.g., RNA viruses like the replicons described below) and other vectors encoding the fusion proteins described herein are used to express these polypeptides in vitro and in vivo. Recombinant nucleic acids are expressed by a variety of conventional techniques (Roberts (1987) Nature 328:731; Schneider (1995) Protein Expr. Purif. 6435: 10; Sambrook, supra Tijssen, supra; Ausubel, supra). Plasmids, vectors, etc., can be isolated from natural sources, obtained from such sources as ATCC or GenBank libraries, or prepared by synthetic or recombinant methods.

The nucleic acids used to practice the invention can be stably or transiently expressed in cells such as episomal expression systems. Selection markers can be incorporated to confer a selectable phenotype on transformed cells. For example, selection markers can code for episomal maintenance and replication such that integration into the host genome is not required. For example, the marker may encode antibiotic resistance, e.g., chloramphenicol, kanamycin, G418, bleomycin, hygromycin) to permit selection of those cells transformed with the desired DNA sequences (Blondelet-Rouault (1997) Gene 190:315-317; Aubrecht (1997) J. Pharmacol. Exp. Ther. 281:992-997).

In Vivo Nucleic Acid Administration

In one embodiment, the nucleic acids encoding the CRT-Class I-binding peptide epitopes are cloned into expression cassettes such as plasmids or other vectors, viruses that can transfect or infect cells in vitro, ex vivo and/or in vivo. A number of delivery approaches are known, including lipid or liposome based gene delivery (Mannino (1988) BioTechniques 6:682-691; U.S. Pat. No. 5,279,833), replication-defective retroviral vectors with desired exogenous sequence as part of the retroviral genome (Miller (1990) Mol. Cell. Biol. 10:4239; Kolberg (1992) J. NIH Res. 4:43; Cornetta (1991) Hum. Gene Ther. 2: 215; Zhang (1996) Cancer Metastasis Rev. 15:385-401; Anderson, Science (1992) 256: 808-813; Nabel (1993) TIBTECH 11: 211-217; Mitani (1993) TIBTECH 11: 162-166; Mulligan (1993) Science, 926-932; Dillon (1993) TIBTECH 11: 167-175; Miller (1992) Nature 357: 455-460).

Expression cassettes can also be derived from viral genomes. Vectors which may be employed include recombinantly modified enveloped or non-enveloped DNA and RNA viruses, examples of which are baculoviridae, parvoviridae, picornoviridae, herpesviridae, poxviridae, adenoviridae, picornnaviridae or alphaviridae. Chimeric vectors may also be employed which exploit advantageous merits of each of the parent vector properties (Feng (1997) Nature Biotechnology 15:866-870). Such viral genomes may be modified by recombinant DNA techniques to include the gene of interest and may be engineered to be replication-deficient, conditionally replicating or replication-competent.

Vectors can be derived from adenoviral, adeno-associated viral or retroviral genomes. Retroviral vectors can include those based upon murine leukemia virus MuLV), gibbon ape leukemia virus (GaLV), simian immunodeficiency virus (SIV), human immunodeficiency virus (HIV), and combinations thereof (Buchscher (1992) J. Virol. 66(5) 2731-2739; Johann (1992) J. Virol. 66 (5):1635-1640 (1992); Sommerfelt (1990) Virol. 176:58-59; Wilson (1989) J. Virol. 63:2374-2378; Miller (1991) J. Virol. 65:2220-2224. Adeno-associated virus (AAV)-based vectors can transduce cells for the in vitro production of nucleic acids and peptides, and be used in in vivo and ex vivo therapy procedures (Okada (1996) Gene Ther. 3:957-964; West (1987) Virology 160: 38-47; Carter (1989) U.S. Pat. No. 4,797,368; Carter et al. WO 93/24641 (1993); Kotin (1994) Human Gene Therapy 5:793-801; Muzyczka (1994) J. Clin. Invst. 94:1351).

In Vivo Administration Using Self-replicating RNA Replicons

In addition to the above-described expression vectors and recombinant viruses, self-replicating RNA replicons can also be used to infect cells or tissues or whole organisms with a fusion protein-expressing nucleic acids of the invention. Thus, the invention also incorporates RNA viruses, includin alphavirus genome RNAs such as from Sindbis virus, Semliki Forest virus, Venezuelan equine encephalitis virus, and the like, that have been engineered to allow expression of heterologous RNAs and proteins. High levels of expression of heterologous sequences such as the fusion polypeptides of the invention, are achieved when the viral structural genes are replaced by the heterologous coding sequences.

These recombinant RNAs are self-replicating ("replicons") and can be introduced into cells as naked RNA or DNA. However, they require trans complementation to be packaged and released from cells as infectious virion particles. The defective helper RNAs contain the cis-acting sequences required for replication as well as an RNA promoter which drives expression of open reading frames. In cells co-transfected with both the replicon and defective helper RNAs, viral nonstructural proteins translated from the replicon RNA allow replication and, transcription of the defective helper RNA to produce the virion's structural proteins (Bredenbeek (1993) J. Virol. 67:6439-6446).

RNA replicon vaccines may be derived from alphavirus vectors, such as Sindbis virus (family Togaviridae) (Xiong (1989) Science 243:1188-1191), Semliki Forest virus (Ying (1999) Nat. Med. 5:823-827) or Venezuelan equine encephalitis virus (Pushko (1997) Virology 239:389401) vectors. These vaccines are self-replicating and self-limiting and may be administered as either RNA or DNA, which is then transcribed into RNA replicons in transfected cells or in vivo (Berglund (1998) Nat. Biotechnol. 16:562-565). Self-replicating RNA infects a diverse range of cell types and allows the expression of the antigen of interest at high levels (Huang (1996) Curr. Opin. Biotechnol. 7:531-535). Additionally, self-replicating RNA eventually causes lysis of transfected cells because viral replication is toxic to infected host cells (Frolov (1996) J. Virol. 70:1182-1190). These vectors therefore do not raise the concern associated with naked DNA vaccines of integration into the host genome. This is particularly important for vaccine development targeting proteins that are potentially oncogenic, such as the adenoviral E7 protein.

In one embodiment, the self-replicating RNA replicon comprises a Sindbis virus self-replicating RNA vector SIN-rep5, as described in detail by Bredenbeek, supra and Herrmann (1998) Biochem. Biophys. Res. Commun. 253: 524-531.

Polypeptides

In other embodiments, the invention is directed to an isolated or recombinant polypeptide comprising at least two domains, wherein the first domain comprises a calreticulin (CRT) polypeptide; and, wherein the second domain comprises an MHC class I-binding peptide epitope. As noted above, the terms "polypeptide," "protein," and "peptide," referring to polypeptides including the CRT, fragments of CRT that bind peptides, and MHC class I-binding peptide epitopes, used to practice the invention, include compositions of the invention that also include "analogues," or "conservative variants" and "mimetics" or "peptidomimetics" with structures and activity that substantially correspond to CRT and MHC class I-binding peptide epitopes. Thus, the terms "conservative variant" or "analogue" or "mimetic" also refer to a polypeptide or peptide which has a modified amino acid sequence, such that the change(s) do not substantially alter the polypeptide's (the conservative variant's) structure and/or activity (ability to bind to "antigenic" peptides, to stimulate an immune response). These include conservatively modified variations of an amino acid sequence, i.e., amino acid substitutions, additions or deletions of those residues that are not critical for protein activity, or substitution of amino acids with residues having similar properties (acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue/substitution): Ala/Gly or Ser; Arg/Lys; Asn/Gin or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or lie; Phe/Met or Leu or Tyr; Ser/Thr; Thr/Ser; Trp/Tyr; Tyr/Trp or Phe; Val/Ile or Leu.

An alternative exemplary guideline uses the groups shown in the Table below. For a detailed description of protein chemistry and structure, see Schulz, GE et al., *Priniciples of Protein Structure*, Springer-Verlag, New York, 1978, and Creighton, T. E., *Proteins: Structure and Molecular Properties*, W.H. Freeman & Co., San Francisco, 1983, which are hereby incorporated by reference. The types of substitutions that may be made in the polypeptides of this invention may be based on analysis of the frequencies of amino acid changes between a homologous protein of different species, defined herein as exchanges within one of the following five groups:

| | | |
|---|---|---|
| 1 | Small aliphatic, nonpolar or slightly polar residues | Ala, Ser, Thr (Pro, Gly); |
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

More substantial changes in biochemical, functional (or immunological) properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g., Leu, Ile, Phe, Val or Ala; (iii) substitution of a Cys residue for (or by) any other residue; (iv) substitution of a residue having an electropositive side chain, e.g., Lys, Arg or His, for (or by) a residue having an electronegative charge, e.g., Glu or Asp; or (v) substitution of a residue having a bulky side chain, e.g., Phe, for (or by) a residue not having such a side chain, e.g., Gly.

One of skill in the art will appreciate that the above-identified substitutions are not the only possible conservative substitutions. For example, for some purposes, all charged amino acids may be considered conservative substitutions for each other whether they are positive or negative. Individual substitutions, deletions or additions that alter, add or delete a single amino acid or a small percentage of amino acids in an encoded sequence can also be considered to yield "conservatively modified variants."

The terms "mimetic" and "peptidomimetic" refer to a synthetic chemical compound that has the necessary structural and/or functional characteristics of a peptide that permits use in the methods of the invention, such as mimicking CRT in interaction with peptides and MHC class I-proteins). The mimetic can be either entirely composed of synthetic, non-natural analogues of amino acids, or, is a combination of partly natural amino acids and partly non-natural analogues. The mimetic can also incorporate any amount of natural amino acid conservative substitutions as long as such substitutions also do not substantially alter the minietics' structure and/or activity. As with conservative variants, routine experimentation will determine whether a mimetic is within the scope of the invention, that its sterochemical structure and/or function is not substantially altered. Peptide mimetics can contain any combination of "non-natural" structural components, typically from three groups: (a) residue linkage groups other than the natural amide bond ("peptide bond"); (b) non-natural residues in place of naturally occurring amino acids; or (c) residues which induce or stabilize a secondary structure, e.g, a β turn, γ turn, β sheet, or α helix conformation. A polypeptide can be characterized as a mimetic when all or some of its residues are joined by chemical bonds other than peptide bonds. Individual peptidomimetic residues can be joined by peptide bonds, other chemical bonds or coupling means, such as glutaraldehyde, N-hydroxysuccinimide esters, bifunctional maleimides, N,N'-dicyclohexylcarbodiimide (DCC) or N,N'-diisopropylcarbodiimide (DIC). Linking groups that are alternatives to peptide bonds include, ketomethylene (—C(—O)—$CH_2$— for —C(=O)—NH—), aminomethylene ($CH_2$—NH), ethylene, olefin (CH=CH), ether ($CH_2$—O), thioether ($CH_2$—S), tetrazole ($CN_4$—), thiazole, retroamide, thioamide, or ester (Spatola (1983) in *Chemistry and Biochemistry of Amino Acids, Peptides and Proteins*, Vol. 7, pp 267-357, *Peptide Backbone Modifications*, Marcell Dekker, NY).

The structure of the polypeptides, peptides, other funcitonal derivatives, including mimetics of the present invention are preferably based on structure and amino acid sequence of CRT, preferably human CRT (McCauliffe (1990) J. Clin. Invest. 86:332-335; Burns (1994) Nature 367:476-480; Coppolino (1998) Int. J. Biochem. Cell Biol. 30:553-558) Human CRT protein (GenBank Accession No. NM 004343), (SEQ ID NO:2) is shown below:

```
  1 MLLSVPLLLG LLGLAVAEPA VYFKEQFLDG DGWTSRWIES KHKSDFGKFV LSSGKFYGDE

61 EKDKGLQTSQ DARFYALSAS FEPFSNKGQT LVVQFTVKHE QNIDCGGGYV KLFPNSLDQT

121 DMHGDSEYNI MFGPDICGPG TKKVHVIFNY KGKNVLINKD IRCKDDEFTH LYTLIVRPDN

181 TYEVKIDNSQ VESGSLEDDW DFLPPKKIKD PDASKPEDWD ERAKIDDPTD SKPEDWDKPE

241 HIPDPDAKKP EDWDEEMDGE WEPPVIQNPE YKGEWKPRQI DNPDYKGTWI HPEIDNPEYS

301 PDPSIYAYDN FGVLGLDLWQ VKSGTIFDNF LITNDEAYAE EFGNETWGVT KAAEKQMKDK

361 QDEEQRLKEE EEDKKRKEEE EAEDKEDDED KDEDEEDEED KEEDEEEDVP GQAKDEL    417
```

Individual synthetic residues and polypeptides incorporating mimetics can be synthesized using a variety of procedures and methodologies well known in the art, e.g., *Organic Syntheses Collective Volumes*, Gilman et al. (dds) John Wiley & Sons, Inc., NY. Polypeptides incorporating mimetics can also be made using solid phase synthetic procedures (e.g., U.S. Pat. No. 5,422,426). Peptides and peptide mimetics of the invention can also be synthesized using combinatorial methodologies. Various techniques for generation of peptide and peptidomimetic libraries are well known e.g., multipin, tea bag, and split-couple-mix techniques (al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234). Modified polypeptide and peptides can be further produced by chemical modification (Belousov (1997) Nucleic Acids Res. 25:3440-3444; Frenkel (1995) Free Radic. Biol. Med. 19:373-380; Blommers (1994) Biochemistry 33:7886-7896).

The peptides can also be synthesized, whole or in part, using conventional chemical synthesis (Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (Roberge (1995) Science 269:202; Merrifield (1997) Methods Enzymol. 289:3-13) and automated synthesis, e.g., using the ABI 431A Peptide Synthesizer (Perkin Elmer) in accordance with the manufacturer' instructions.

In one embodiment of the invention, peptide-binding fragments or "sub-sequences" of CRT are used. In another embodiment, other peptides that bind to MHC proteins, preferably MHC Class I proteins, are used. Such peptides can be derived from any polypeptide, particularly, from a known pathogen, or it can be entirely synthetic). Methods for determining whether, and to what extent, a peptide binds to a CRT or a CRT fragment, or an MHC protein are routine in the art (Jensen (1999) Immunol. Rev. 172:229-238; Zhang (1998) J. Mol. Biol. 281:929-947; Morgan (1997) Protein Sci 6:1771-1773; Fugger (1996) Mol. Med. 2:181-188; Sette (1994) Mol. Immunol. 31:813-822; Elvin (1993) J. Immunol. Methods 158:161-171; U.S. Pat. Nos. 6,048,530; 6,037,135; 6,033,669; 6,007,820).

Formulation and Administration of Pharmaceutical Compositions

In various embodiments of the invention, polypeptides, nucleic acids, expression cassettes, cells, and particles, are administered to an individual as pharmacological compositions in amounts sufficient to induce an antigen-specific immune response (e.g., a CTL response, see Example, below) in the individual.

Pharmaceutically acceptable carriers and formulations for nucleic acids, peptides and polypeptides are known to the skilled artisan and are described in detail in the scientific and patent literature, see e.g., the latest edition of Remington's Pharmaceutical Science, Maack Publishing Company, Easton, Pa. ("Remington's"); Banga; Putney (1998) Nat. Biotechnol. 16:153-157; Patton (1998) Biotechniques 16:141-143; Edwards (1997) Science 276: 1868-1871; U.S. Pat. Nos. 5,780,431; 5,770,700; 5,770,201.

The nucleic acids and polypeptides used in the methods of the invention can be delivered alone or as pharmaceutical compositions by any means known in the art, e.g., systemically, regionally, or locally; by intraarterial, intrathecal (IT), intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa). Actual methods for delivering compositions will be known or apparent to those skilled in the art and are described in detail in the scientific and patent literature, see e.g., Remington's.

The pharmaceutical compositions can be administered by any protocol and in a variety of unit dosage forms depending upon the method and route and frequency of administration, whether other drugs are being administered, the individual's response, and the like. Dosages for typical nucleic acid, peptide and polypeptide pharmaceutical compositions are well known to those of skill in the art. Such dosages may be adjusted depending on a variety of factors, e.g., the initial responses (e.g., number and activity of CTLs induced, tumor shrinkage, and the like), the particular therapeutic context, patient health and tolerance. The amount of pharmaceutical composition adequate to induce the desired response is defined as a "therapeutically effective dose." The dosage schedule and amounts effective for this use, i.e., the "dosing regimen," will depend upon a variety of factors, including, e.g., the diseases or conditions to be treated or prevented by the immunization, the general state of the patient's health, the patient's physical status, age, pharmaceutical formulation and concentration of pharmaceutical composition, and the like. The dosage regimen also takes consideration pharmacokinetics, i.e., the pharmaceutical composition's rate of absorption, bioavailability, metabolism, clearance, and the like (Remington). Dosages can be determined empirically, e.g., by assessing the abatement or amelioration of symptoms, or, by objective criteria, e.g., measuring levels of antigen-specific CTLs. As noted above, a single or multiple administrations can be administered depending on the dosage and frequency as required and tolerated by the patient. The pharmaceutical compositions can be administered alone or in conjunction with other therapeutic treatments, or, as prophylactic immunization.

Ex Vivo Treatment and Re-administration of APCs

In various embodiments of the invention, the nucleic acids and polypeptides of the invention are introduced into the individual by ex vivo treatment of antigen presenting cells (APCs), followed by administration of the manipulated APCs. In one embodiment, APCs are transduced (transfected) or infected with fusion protein-encoding nucleic acids of the invention; afterwards, the APCs are administered to the individual. In another embodiment, the APCs are stimulated with fusion proteins of the invention (purified or as a cell lysate from cells transfected and expressing a recombinant fusion protein in vivo). Afterward this "pulsing, the APCs are administered to the individual.

The fusion proteins can be in any form, e.g., as purified or synthetic polypeptides, as crude cell lysates (from transfected cells making recombinant fusion protein), and the like. The APC can be an MHC-matched cell (a tissue-typed cell). The APC can be a tissue-cultured cell or it can be an APC isolated from the individual to be treated and re-administered after ex vivo stimulation. Any APC can be used, as described above. Methods of isolating APCs, ex vivo treatment in culture, and re-administration are well known in the art (U.S. Pat. Nos. 5,192,537; 5,665,350; 5,728,388; 5,888,705; 5,962,320; 6,017,527; 6,027,488).

Kits

The invention provides kits that contain the pharmaceutical compositions of the invention, as described above, to practice the methods of the invention. In alternative embodiments, the kits can contain recombinant or synthetic chimeric polypeptides comprising a first domain comprising an ER chaperone polypeptide and a second domain comprising an antigenic peptide, e.g., a CRT-Class I-binding peptide epitope fusion protein; or, the nucleic acids encoding them, e.g., in the form of naked DNA (e.g., plasmids), viruses (e.g. alphavirus-derived "replicons" including Sindbis virus replicans) and the like. The kit can contain instructional material teaching methodologies, e.g., means to administer the compositions used to practice the invention, means to inject or infect cells or patients or animals with the nucleic acids or polypeptides of the invention, means to monitor the resultant immune response and assess the reaction of the individual to which the compositions have been administered, and the like.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

Administration of CRT-Class I-binding Peptide Epitopes Enhance Generation of an Antigen-specific Cytotoxic T Lymphocyte (CTL) Response The following example describes studies which demonstrate that the compositions and methods of the invention are effective for enhancing antigen-specific cytotoxic T lymphocyte (CTL) responses.

These studies used a DNA vaccine comprising encoding sequence for the fusion protein including both calreticulin (CRT) and a Class I polypeptide-binding peptide epitope, wherein the epitope was a model antigen, the human papilloma virus-16 E7 polypeptide (HPV-16 E7). The anti-tumor effects mediated by E7-specific immune responses and the vaccine-stimulated anti-angiogenesis effects in vaccinated mice were evaluated. C57BL/6 mice that were vaccinated intradermally with DNA vaccines comprising chimeric calreticulin/E7 (CRT/E7) fusion genes exhibited dramatically increased E7-specific CD8+ T cell (CTL) precursors, tumor protection, and tumor treatment compared to DNA vaccines containing wild-type E7 or CRT genes alone. Furthermore, treatment of C57BL/6 mice or nude mice with either CRT DNA or chimeric CRT/E7 DNA led to reduction of lung metastatic nodules and inhibition of angiogenesis within the lung nodules. These results indicate that the linkage of the CRT gene to an antigen gene may greatly enhance the potency of DNA vaccines to elicit anti-tumor effects through both a significant enhancement of antigen-specific $CD8^+$ T cell (CTL) immune responses and anti-angiogenesis effects.

Plasmid DNA Constructs and Preparation: The generation of HPV-16 E7-expressing pcDNA3 plasmid was done as described by Chen (2000) Cancer Res. 60:1035-1042; see also Chen (2000) Vaccine 18:2015-2022; Ji (1999) Hum. Gene Ther. 10:2727-2740; Chen (1999) Gene Ther. 6:1972-1981; Ji (1998) Int. J. Cancer 78:41-45. See also, e.g., Seedorf (1987) EMBO J. 6:139-144; U.S. Pat. Nos. 5,629,161; 5,501,947; 5,547,846; 5,180,806; 4,777,239. See GenBank Accession No. AF125673 (Jun. 1, 1999) describing the complete HPV-16 genome and the HPV-16 E7 protein, having the sequence (SEQ ID NO:5)
MHGDTPTLHEYMLDLQPETTDLYCYEQLNDSSEEEDEIDGPAGQAEPDRA

HYNIVTFCCKCDSTLRLCVQSTHVDIRTLEDLLMGTLGIVCPICSQKP

For the generation of plasmid encoding the full length of rabbit calreticulin (there is more than 90% homology between rabbit, human, mouse, and rat calreticulin), pcDNA3-CRT, the DNA fragment encoding this protein was first amplified with PCR using conditions as described in Chen (2000) Cancer Res., supra, using rabbit calreticulin cDNA template (Michalalk (1999) Biochem J. 344 Pt 2:281-292), provided by Dr. Marek Michalak, University of Alberta, Edmonton, Canada, and a set of primers: 5'-cegggtctagaatgctgctccctgtgccgct-3' (SEQ ID NO:6) and (SEQ ID NO:7) 5'-ccggagatctcagctcgtccttggcctggc-3'. The amplified product was then digested with the restriction digest enzymes XbaI and BamHI and further cloned into the XbaI and BamHI cloning sites of pcDNA3 vector (Invitrogen, Carlsbad, Calif.). For the generation of pcDNA3-CRT/E7, the E7 DNA was amplified by PCR using pcDNA3-E7 as a DNA template and a set of primers: 5'-ggggaattcatggagata-caccta-3' (SEQ ID NO:7) and 5'-ggtggatccttgagaacagatgg-3' (SEQ ID NO:8). The amplified E7 DNA fragment was then digested with BamHI and further cloned into the BamHI cloning sites of pcDNA3-CRT vector. The orientation and accuracy of these constructs was confirmed by DNA sequencing.

Plasmid DNA with CRT, E7 or CRT/E7 gene insert and the "empty" plasmid vector were transfected into subcloning-efficient DH5™ cells (Life Technologies, USA). The DNA was then amplified and purified using double CsCl purification (BioServe Biotechnologies, Laurel, Md.). The integrity of plasmid DNA and the absence of *Escherichia coli* DNA or RNA were checked in each preparation using 1% agarose gel electrophoresis. DNA concentration was determined by the optical density, measured at 260 nm. The presence of inserted E7 fragment was confirmed by restriction enzyme digestion and gel electrophoresis.

Cell Lines: The production and maintenance of TC-1 cells was done as described in Lin (1996) Cancer Res. 56:21-26. On the day of tumor challenge, TC-1 cells were harvested by trypsinization, washed twice with 1× Hanks buffered salt solution (HBSS) and finally resuspended in 1× HBSS to the designated concentration for injection. A human embryonic kidney 293 cell line expressing the $D^b$ and $K^b$ (293 $D^b$, $K^b$) (Bloom (1997) J. Exp. Med. 185:453-459) was provided by Dr. J C Yang (NCI, NIH, Bethesda, Md.). It was grown in DMEM medium containing 10% heat-inactivated fetal calf serum, 0.3% glutamine, 0.01 M HEPES, 100 U/ml penicillin, 100 μg G418.

Mice: 6- to 8-week-old female C57BL/6 mice from the National Cancer Institute (Frederick, Md.) were purchased and kept in the oncology animal facility of the Johns Hopkins Hospital (Baltimore, Md.). To characterize the effect of anti-angiogenesis, in vivo tumor treatment experiments in the absence of immune effectors were conducted using BALB/c nu/nu 6-week old female mice from the National Cancer Institute (Frederick, Md.). All animal procedures were performed according to approved protocols and in accordance with recommendations for the proper use and care of laboratory animals.

DNA Vaccination: Preparation of DNA-coated gold particles and gene gun particle-mediated DNA vaccination was performed using a helium-driven gene gun (Bio-Rad, Hercules, Calif.) according as described by Chen (2000) Cancer Res., supra. Briefly, DNA coated gold particles (1 or 4 μg DNA/bullet) were delivered to the shaved abdominal region of the mice using the helium-driven gene gun with a discharge pressure of about 400 p.s.i.

Intracytoplasmic Cytokine Staining and Flow Cytometry Analysis: Splenocytes from naive or vaccinated groups of mice were incubated either with the E7 peptide (amino acid (aa) residues 49 to 57) that contains MHC class I epitope (Feltkamp (1993) Eur. J. Immunol. 23:2242-2249) for detecting E7-specific CD8+ T cell precursors, or, the E7 peptide (aa 30 to 67) that contains IC class II peptide (Tindle (1991) Proc. Natl. Acad. Sci. USA 88:5887-5891) for detecting E7-specific CD4+ T helper cell precursors. The E7 peptide was added at a concentration of 1 μg/ml for aa 49-57 and 10 μg/ml for aa 30-67 for 20 hours. Golgistop™ (Pharmigen, San Diego, Calif.) was added 6 hours before harvesting the cells from the culture. Cells were then washed once in FACScan™ buffer and stained with phycoerythrin (PE)-conjugated monoclonal rat anti-mouse CD8 or CD4 antibody (PharMingen, San Diego, Calif.). Cells were subjected to intracellular cytokine staining using the Cytofix/Cytoperm™ kit according to the manufacturer's instructions (PharMingen). FITC-conjugated anti-IFN-gamma and anti- IL4 antibodies and the immunoglobulin isotype control antibody (rat IgG1) were all purchased from PharMingen. Flow cytometry analysis was performed on a Becton Dickinson FACScan™ with CELLQuest™ software (Becton Dickinson Immunocytometry System, 31 Mountain View, Calif.).

ELISA for anti-E7 Antibody: Anti-HPV 16 E7 antibodies in the sera were determined by a direct ELISA as described by Wu (1995) Proc. Natl. Acad. Sci. USA 92:11671-11675. Briefly, a 96-microwell plate was coated with 10.5 µg/ml bacteria-derived HPV-16 E7 proteins and incubated at 40° C. overnight. The wells were then blocked with PBS containing 20% fetal bovine serum. Sera were prepared from the mice on day 14 post-immunization, serially diluted in 1× PBS, added to the ELISA wells, and incubated at 37° C. for 2 hr. After washing with 1×PBS containing 0.05% Tween-20, the plate was incubated with 1/2000 dilution of a peroxidase-conjugated rabbit anti-mouse IgG antibody (Zymed, San Francisco, Calif.) at room temperature (RT) for one hour. The plate was washed 6 times, developed with TMB (Pierce, Rockford, Ill.), and stopped with 1M $H_2SO4$. The ELISA plate was read with a standard ELISA reader at 450 nm.

In Vivo Tumor Protection Experiments: For the tumor protection experiment, mice (5 per group) were vaccinated via gene gun with 2 µg of CRT DNA, E7 DNA, CRT/E7 DNA or unvaccinated. One week later, the mice were boosted with the same regimen as the first vaccination. One week after the last vaccination, mice were subcutaneously challenged with $5 \times 10^4$ TC-1 cells/mouse in the right leg. Mice were monitored for evidence of tumor growth by palpation and inspection twice a week until they were sacrificed at day 60.

In Vivo Tumor Treatment Experiments: C57BL/6 Mice (5 each group) were intravenously challenged with $1 \times 10^4$ cells/mouse TC-1 tumor cells via tail vein on day 0. Three days after challenge with TC-1 tumor cells, mice were given 2 µg of CRT DNA, E7 DNA, CRT/E7 DNA via gene gun or unvaccinated. One week later, these mice were boosted with the same regimen as the first vaccination. Mice were monitored twice a week and sacrificed on day 21. The number of pulmonary metastatic nodules of each mouse was evaluated and counted by experimenters blinded to the sample identity.

Nude (BALB/c nu/nu) mice (5 each group) were intravenously challenged with $1 \times 10^4$ cells/mouse TC-1 tumor cells via tail vein on day 0. Two days (D2) after challenge with TC-1 tumor cells, mice were given 16 µg of CRT DNA, E7 DNA, CRT/E7 DNA, or the empty plasmid without insert via gene gun. On day 9 and day 16, these mice were boosted with the same regimens as the first vaccination. The mice were sacrificed on day 21. The pulmonary nodules of each mouse were evaluated and counted by experimenters blinded to sample identity.

In Vivo Antibody Depletion Experiments: In vivo antibody depletions were done as described by Lin (1996) Cancer Res. 56:21-26. Briefly, mice were vaccinated with 2 µg CRT/E7 DNA via gene gun, boosted one week later, and challenged with $5 \times 10^4$ cells/mouse TC-1 tumor cells. Depletions were started one week prior to tumor challenge. MAb GK1.5 (Dialynas (1983) Immunol. Rev. 74: 29-56) was used for CD4 depletion, MAb 2.43 (Sarmiento (1980) J. Immunol. 125: 2665) was used for CD8 depletion, and MAb PK136 (Koo (1986) J. Immunol. 137:3742-3747) was used for NK1.1 depletion. Flow cytometry analysis revealed that >99% of the appropriate lymphocytes subset were depleted while maintaining normal levels of other subsets. Depletion was terminated on day 40 after tumor challenge.

Generation of Dendritic Cells: Dendritic cells (DCs) were generated by culture of bone marrow cells in the presence of GM-CSF as described by Fernandez (1999) Nat. Med. 5:405-411). Briefly, bone marrow was collected from the femurs and tibias of mice. Erythrocytes were lysed, and the remaining cells were passed through a nylon mesh to remove small pieces of bone and debris. The cells were collected and $1 \times 10^6$ cells/ml were placed in 24-well plates in RMPI 1640, supplemented with 5% FCS, 2 nM (-mercaptoethanol, 1% nonessential amino acids, 100 U/ml penicillin and 100 (g/ml streptomycin (Life Technologies, Rockville, Md.), and 100 U/ml GM-CSF (PharMingen, San Diego, Calif.). Two-thirds of the medium was replaced every 2; days, and non-adherent cells were harvested on day 7. The collected cells were characterized using flow cytometry analysis for DC markers as previously described (25).

Generation of E7-Specific CD8+ T Cell Lines: E7-specfic CD8+ cell lines were generated by immunizing female C57BL/6 (H-2b) mice by intraperitoneal injection of vaccinia E7 expressing expression vector (a lysosome-associated membrane protein 1 (LAMP-1) coding sequence was fused to HPV-E7 coding sequence to construct a chimeric DNA, designated Sig/E7/LAMP-1, as discussed by Ji (1999) Hum. Gene Ther. 10:2727-2740). Splenocytes were harvested on day 8. For initial in vitro stimulation, splenocytes were pulsed with IL2 at a concentration of 20 U/ml and 1 TM E7 peptide (amino acids 49-57 of SEQ ID NO:4) for 6 days. Propagation of the E7-specific CTL cell line was performed in 24-well plates by mixing (2 ml/well) $1 \times 10^6$ splenocytes containing E7-specific CTLs with $3 \times 10^6$ irradiated splenocytes and pulsing them with IL-2 at a concentration of 20 U/ml and 1 TM E7 peptide (amino acids 49-57).

This procedure was repeated every 6 days. The specificity of the E7 CTL line was characterized by the CTL assay. Flow cytometry was performed to demonstrate the expression of the CD8 marker.

CTL Assay using Transfected 293 $D^b K^b$ Cells as Target Cells. CTL assays were performed in 96-well round-bottom plates as described by Corr (1999) J. Immunol. 163:4721-4727. Cytolysis was determined by quantitative measurements of lactate dehydrogenase (LDH). Transfected 293 $D^b K^b$ cells were used as target cells while E7-specific CD8+ T cells served as effector cells. $5 \times 10^6$ 293 $D^b K^b$ cells were transfected with 20 Tg of pcDNA3 (empty plasmid), E7, CRT, or CRT/E7 DNA vaccines via lipofectamine 2000™ (Life Technologies, Rockville, Md.) according to manufacturer's protocol. The 293 $D^b K^b$ cells were collected 40-44 hr after transfection. The levels of E7 protein expression as determined by ELISA were similar in E7 and CRT/E7 transfected 293 $D^b K^b$. CTL assays were performed with effector cells and targets cells ($1 \times 10^4$ per well) mixed together at various ratios (1:1, 3:1, 9:1, and 27:1) in a final volume of 200 Tl. After a 5 hr incubation at 37° C., 50 Tl of the cultured media were collected to assess the amount of LDH in the cultured media using CytoToX™ assay kits (Promega, Madison, Wis.) according to the manufacturer's protocol. The percentage of lysis was calculated from the following equation: $100 \times (A-B)/(C-D)$ where A is the reading of experimental-effector signal value, B is the effector spontaneous background signal value, C is maximum signal value from target cells, D is the target spontaneous background signal value.

CTL Assay Using DCs Pulsed with Lysates of Transfected 293 Cells as Target Cells: CTL assays using dendritic cells (DCs) pulsed with cell lysates as target cells were performed using a protocol similar to that described by Uger (1998) J. Immunol. 160:1598-1605. Briefly, $5 \times 10^6$ 293 $D^b K^b$ cells were first transfected with 20 Tg of pcDNA3 (empty plasmid), E7, CRT, or CRT/E7 DNA vaccines via lipofectamine 2000™ (Life Technologies, Rockville, Md.) according to manufacturer's protocol. The transfected 293 $D^bK^b$ cells were collected 40-44 hr after transfection and then treated with three cycles of freeze-thaw. The protein concentration was determined using the BioRad protein assay (Bio-Rad, Hercules, Calif.) according to vendor's protocol. The quantity of E7 protein was determined using ELISA and the cell lysates from E7 or CRT/E7 DNA transfected 293 $D^bK^b$ cells were standardized for E7 protein concentration. The DCs were used as target cells and prepared by pulsing 1 million DCs with different concentrations of cell lysates (50 Tg/ml, 10 Tg/ml, 2 Tg/ml and 0.4 Tg/ml) in a final volume of 2 ml for 16-20 hrs. E7-specific CD8+ T cells were used as effector cells. CTL assays was performed at fixed E/T (9/1) ratio with $9\times10^4$ of E7-specific T cells mixed with $1\times10^4$ of prepared DCs in a final volume of 200 Tl. Cytolysis was determined by quantitative measurements of LDH as described above.

Histologic and immunohistochemical studies: Paraffin blocks of the lung nodules from vaccinated mice were generated and sectioned in 6 Tm slices and deparaffinized. Hematoxylin and eosin staining was performed for routine light microscopic examination and unstained sections were prepared for immunohistochemical study. Mouse anti-CD31 monoclonal antibodies (DAKO, Capinteria, Calif.) were used for the detection of intratumoral microvessels. Immunohistochemical staining was performed on the sections from both specimens using the protocol as described by Huang (1999) Hum. Pathol. 30: 587-591. Microvessel density (MVD) was measured as described by Cheng (1999) Cancer 85:651-657. Briefly, stained slides were examined at low-power magnification (40× and 100× total magnification) to identify the areas of highest neovascularization (so-call hot spots) in each tumor. In each section, the three most vascularized areas were chosen. Microvessel counts were obtained at 200× magnification (20× objective and 10× ocular (Olympus BH-2 microscope), 0.74 mm² per field with the field size measured with an ocular micrometer) and the mean number in the three fields for each tumor was calculated, referred to as the microvessel density (MVD) count. Large vessels with thick muscular walls and lumina greater than appropriately eight blood cells were excluded from the count. All measurements were performed by a single pathologist blinded to the sample identity.

Generation and Characterization of the CRT/E7 Fusion DNA Vaccine: A schematic diagram of the constructs of calreticulin (CRT), E7, and calreticulin/E7 (CRT/E7) is presented in FIG. 1. All of the constructs have been confirmed by DNA sequencing. To demonstrate the expression of E7 protein in E7-containing constructs, a Western blot analysis using lysates of 293 $D^bK^b$ cells transfected with various E7-containing DNA constructs was performed. 293 $D^bK^b$ cells transfected with wild-type E7 showed a 30 kD band corresponding to HPV-16 E7. In addition, 293 $D^bK^b$ cells transfected with CRT/E7 showed a band corresponding to chimeric CRT/E7 protein. No visible bands were observed in the negative controls, 293 $D^bK_b$ transfected with either calreticulin or empty plasmid.

Vaccination with CRT/E7 Fusion DNA Significantly Enhances the Numbers of E7-Specific CD8+ T Cells: CD8+ T lymphocytes (CTLs) are one of the most crucial effectors for inducing anti-tumor immunity. To determine the quantity of E7-specific CD8+ T cell precursors induced after in vivo administration (to mice) of the CRT/E7 DNA vaccine of the invention, intracellular cytokine staining was used as described by Ji (1999) Human Gene Therapy 10:2727-2740.

Intracellular cytokine staining is a sensitive functional assay used to measure IFN-gamma (IFN-K) production at the single-cell level, which can thus be applied to quantify antigen-specific CD8+ T cells. The results of the flow cytometry analysis (performed as discussed above) is shown in the two-dimensional histogram in FIG. 2A. As summarized in FIG. 2B, mice vaccinated with CRT/E7 DNA induced the highest number of E7-specific IFN-gamma expressing/CD8+ T cell precursors ($204/3.5\times10^5$ splenocytes), whereas mice vaccinated with E7 DNA induced fewer precursors ($47/3.5\times10^5$ splenocytes) (p<0.01). CRT/E7 chimeric construct immunization led to a 5-fold increase in the number of E7-specific CD8+ T cell precursors. These results also indicated that fusion of E7 to CRT (i.e., expression as a fusion protein) was required for enhancement of CD8+ T cell activity, since vaccination with two vectors, one expressing only CRT mixed with one expressly only E7 ("CRT+E7" on FIG. 2B) did not induce enhancement of CD8+ T cell activity.

Vaccination with CRT/E7 Fusion DNA Does Not Enhance E7-Specfic CD4+ T Cell-Mediated Immune Responses: To examine the generation of E7-specific CD4+ ("helper") T precursor cells and cytokine profiles induced by each of these vaccines, we performed double staining for CD4 surface marker and intracellular IFN-K+ on splenocytes from immunized mice, followed by flow cytometry analysis. The splenocytes from immunized mice were cultured in vitro with E7 peptide (aa 30-67) overnight and stained for both CD4 and intracellular IFN-K+. The E7 peptide (aa 30-67) contains a major T helper epitope in the E7 open reading frame protein of HPV-16 (Tindle (1991) Proc Natl. Acad. Sci. USA 88:5887-5891. The percentage of IFN-K+ secreting CD4+ T cells was analyzed using flow cytometry. Mice vaccinated with CRT/E7 chimeric constructs induced a similar number of CD4+ IFNK+ double positive cells compared to mice vaccinated with wild-type E7 DNA ($25/3.5\times10^5$ splenocytes versus $20/3.5\times10^5$ splenocytes, p>0.05) or other DNA groups. There was no significant difference in the number of E7-specific CD4+IFNK+ cells observed using flow cytometry staining among naive mice or mice vaccinated with empty plasmid, CRT, E7, CRT+E7, or CRT/E7 constructs.

The numbers of IL-4-secreting E7-specific CD4+ T cells in mice vaccinated with various DNA vaccines was also assessed. IL4-secreting activated mouse splenocytes (MiCK-2™, PharMingen, San Diego, Calif.) were used as positive controls to ensure the success of intracellular IL-4 staining for this study. The specificity of the IL-4 staining was demonstrated by the absence of CD4+ IL-4+T cells when the IL-4 antibody was omitted. No significant CD4+ IL-4+double-positive cells were identified in mice vaccinated with CRT/E7, CRT, wild type E7 DNA, plasmid DNA vaccination or in naive mice without vaccination. In addition, no significant variation was observed in the frequency of IL-4-secreting CD4+ IL-4+T cells from the different vaccination groups.

Figure 3:
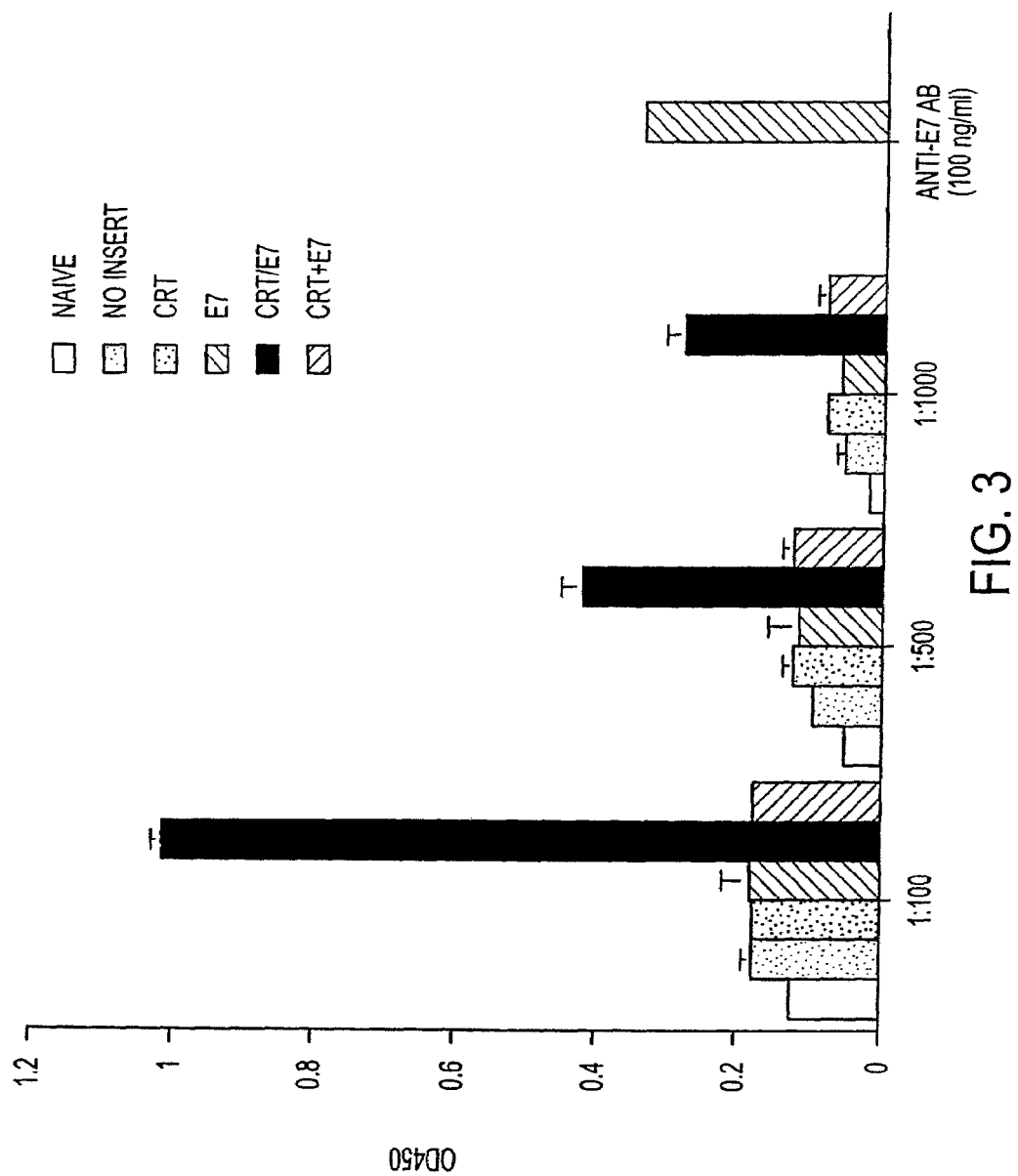
FIG. 3 shows a schematic summary of data showing the quantity of anti-HPV 16 E7 antibodies in the sera of vaccinated mice as determined by a direct ELISA two weeks after the last vaccination with construct only and constructs encoding CRT alone, E7 alone, CRT/E7 fusion protein, and, a mixture of two construct expressing CRT and E7 individually, as discussed in Example 1, below.

Vaccination with CRT/E7 induced Higher Titers of E7-Specific Antibodies: The quantity of anti-HPV 16 E7 antibodies in the sera of vaccinated mice was determined by a direct ELISA two weeks after the last vaccination. As shown in FIG. 3, the CRT/E7 vaccinated group induced the highest titers of anti-E7 antibodies in the sera of mice compared to the other vaccinated groups (P<0.01). This result showed that mice vaccinated with CRT/E7 chimeric construct of the invention induced significantly higher E7-specific antibody responses.

Figure 4:
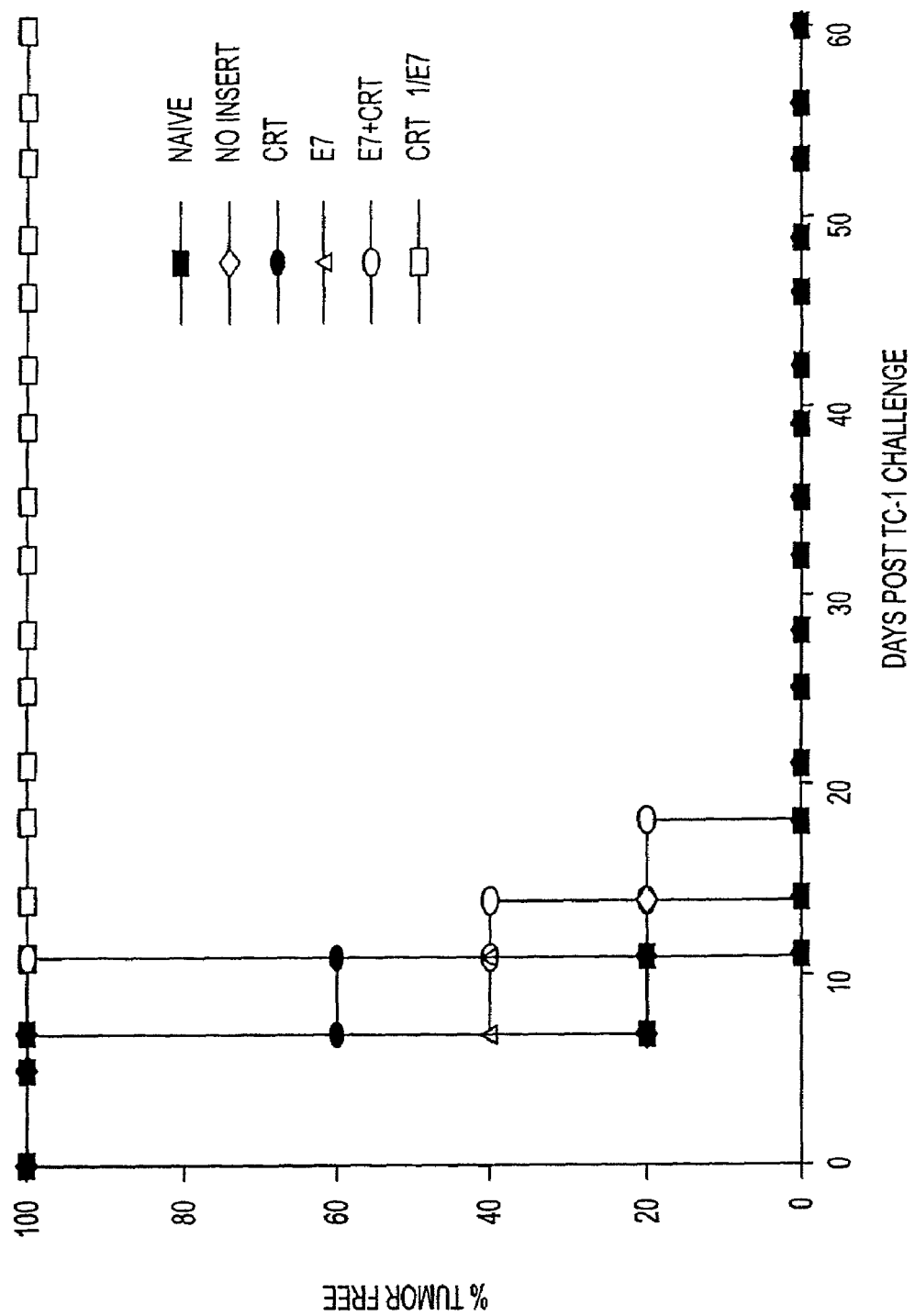
FIG. 4 shows a schematic summary of in vivo tumor protection experimental data in which mice were vaccinated with various DNA vaccine constructs and later challenged with E7-expressing tumor, as discussed in Example 1, below.

Vaccination with CRT/E7 Chimeric Construct Enhances Protection of mice Against the Growth of TC-1 Tumors: To determine whether vaccination with the various DNA vaccine constructs protects mice against E7-expressing tumors, in vivo tumor protection experiments were performed. Mice were vaccinated with 2 Tg naked DNA/mouse via gene gun and boosted with the same dose one week later. Mice were then challenged with $5 \times 10^4$ TC-1/mouse subcutaneously in the right leg 7 days after the last vaccination. As shown in FIG. 4, 100% of those receiving CRT/E7 chimeric construct vaccination remained tumor-free 60 days after TC-1 challenge. In contrast, all of the unvaccinated mice and mice receiving empty plasmid, CRT, wild-type E7, or wild type E7+CRT DNA developed tumor growth within 15 days after tumor challenge. These results also indicated that fusion of E7 to calreticulin was required for antitumor immunity, since constructs expressing only calreticulin mixed with constructs expressing only E7 ("CRT+E7" in FIG. 4) does not induce enhancement of antitumor immunity. Therefore, the CRT/E7 chimeric constructs of the invention significantly enhanced protection against the growth of TC-1 tumors.

Figure 5:
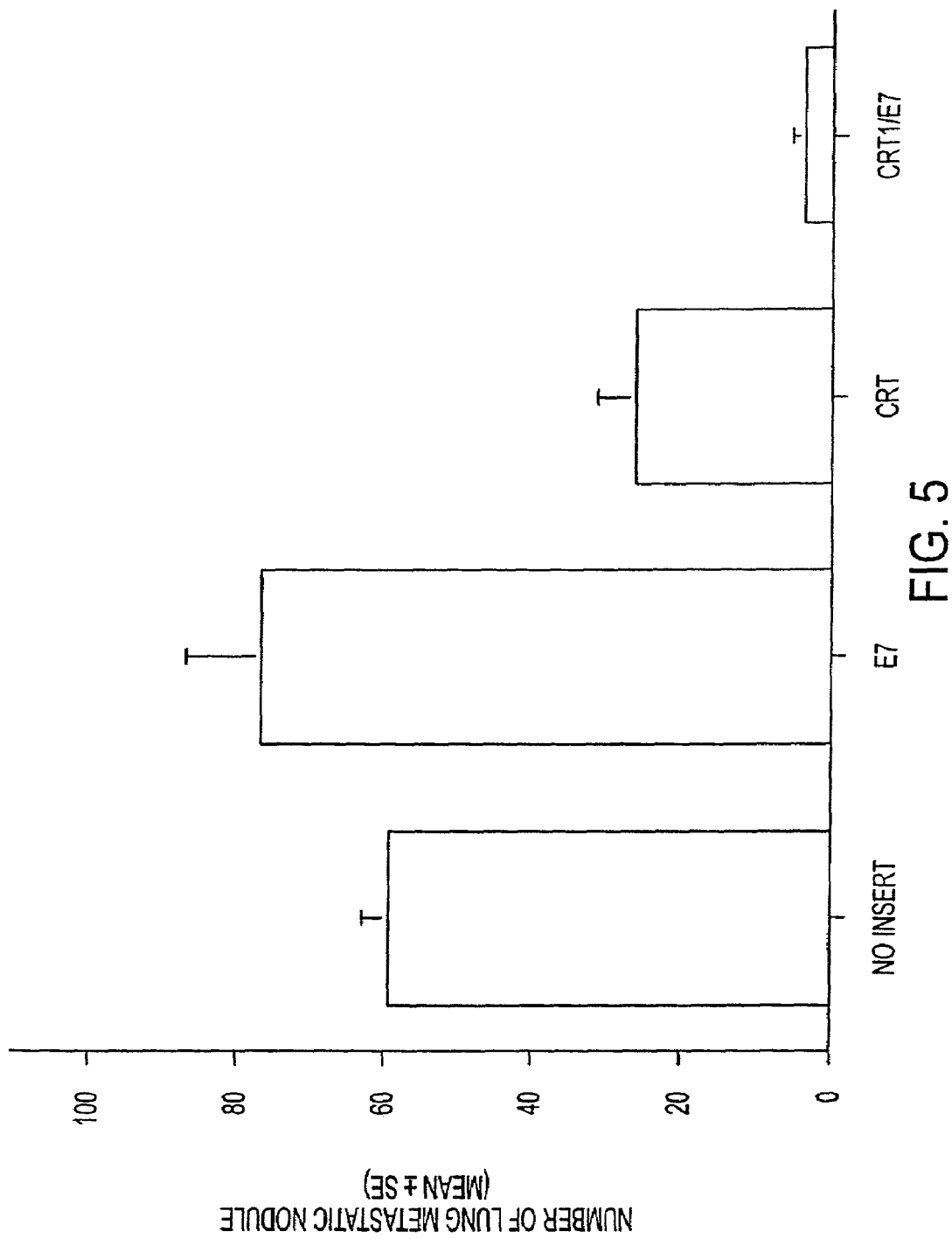
FIG. 5 shows a schematic summary of data from experiments in which mice were first injected with tumor cells, followed by vaccination with various naked DNA constructs (including a one week booster after day 1 of vaccination); thereafter the mean number of pulmonary nodules was assessed; data are expressed as mean number of pulmonary metastatic tumor nodules +SEM as a function of days post tumor cell challenge, as discussed in Example 1, below.

Vaccination with CRT/E7 Chimeric Construct Eradicates Established E7-expressing Tumors in the Lungs: To determine the therapeutic potential of a chimeric CRT/E7 DNA construct in treating TC-1 tumor metastases in the lungs, C57BL/6 mice were first challenged with $1 \times 10^4$ TC-1 tumor cells per mouse via intravenous tail vein injection (lung metastasis model) Ji (1998) Int. J. Cancer 78:41-45. Mice were then treated with 2 Tg naked DNA via gene gun seven days later and boosted with the same dose 1 week later. Mice were then sacrificed 30 days after tumor challenge. As shown in FIG. 5, mice vaccinated with CRT/E7 chimeric construct revealed the lowest mean number of pulmonary nodules (4.0+1.6) compared to mice vaccinated with wild-type E7 DNA only (77.6+9.8), or calreticulin DNA only (26.4+4.9) (one-way ANOVA, P<0.001). Data are expressed as mean number of pulmonary metastatic tumor nodules +SEM. Interestingly, mice vaccinated with wild-type calreticulin DNA displayed a lower mean number of nodules than mice receiving wild-type E7 DNA or no vaccination (one-way ANOVA, P<0.001). Since mice vaccinated with CRT alone did not induce E7-specific T cell immune responses, the therapeutic effects (lower number of lung metastatic nodules) observed with CRT alone may be caused by a CRT-mediated anti-angiogenesis effect.

CD8+ T Cells But Not CD4+ T cells or NK cells are Essential for the Anti-tumor Effect Induced by, the CRT/E7 Chimeric DNA Vaccine of the Invention: To determine the subset of lymphocytes that are important for the rejection of E7-positive tumor cells, we performed in vivo antibody depletion experiments. Depletion of lymphocyte subsets was assessed on the day of tumor injection, and weekly thereafter by flow cytometry analysis of spleen cells. More than 99% depletion of the appropriate subset was achieved with normal levels of other lymphocyte subsets. All naive mice and all mice depleted of CD8+ T cells grew tumors within about 14 days after tumor challenge. In contrast, all of the non-depleted mice and all of the mice depleted of CD4+ T cells or NK1.1 cells remained tumor-free 60 days after tumor challenge. These results demonstrate that CD8+ T cells are essential for the anti-tumor immunity induced by the CRT/E7 chimeric vaccine of the invention.

Figure 6:
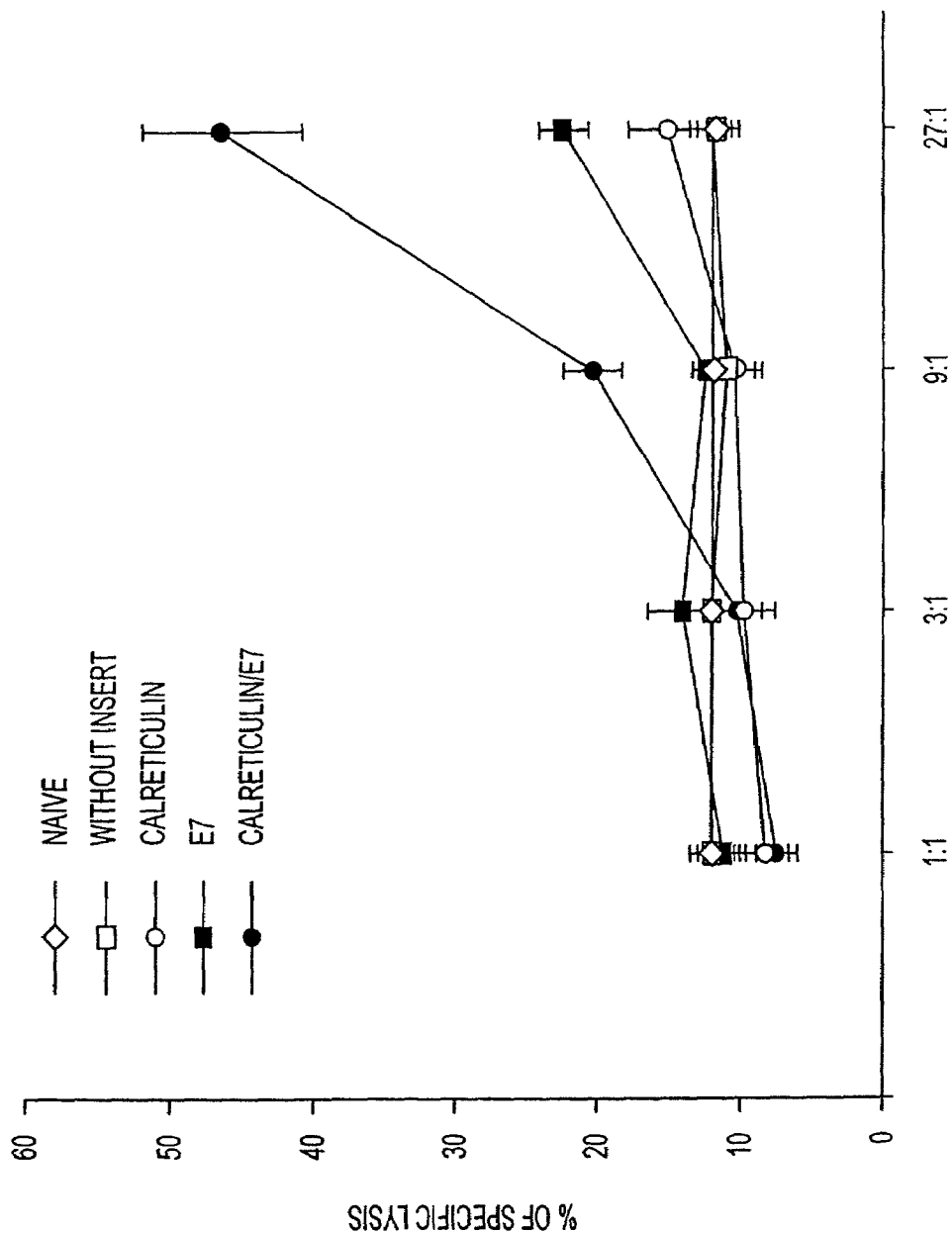
FIG. 6 shows a schematic summary of data of CTL assays using Db-restricted E7-specific CD8+ T cells as effector cells against 293 $D^bK^b$ target cells transfected with various naked DNA constructs, as discussed in Example 1, below.

Enhanced Presentation of E7 Through the MHC Class I Pathway is Cells Transfected with CRT/E7 DNA: As discussed above, mice vaccinated with the CRT/E7 chimeric construct of the invention induced the highest number of E7-specific CD8+ T cell precursors. In order to determine the mechanism that accounted for this effect, it was determined if there was enhanced MHC class I presentation of E7 in target cells, in this case, human embryonic kidney 293 cells expressing Db and Kb transfected with the CRT/E7 fusion protein encoding chimeric DNA. CTL assays with Db-restricted E7-specific CD8+ T cells as effector cells were used to determine if target cells (293 $D^bK^b$ cells) transfected with a CRT/E7 construct can be killed more efficiently than 293 $D^bK^b$ cells transfected with only wild type E7. 293 $D^bK^b$ cells were used as target cells because they have been shown to have stable transfection efficiency, whereas dendritic cells are not transfected as readily in vivo. In addition, the level of E7 expression in 293 $D^bK^b$ cells is similar among cells transfected with different E7-containing DNA constructs. CTL assays were performed using naïve 293 $D^bK^b$ cells and 293 $D^bK^b$ cells transfected with empty plasmid, CRT, E7, or chimeric CRT/E7 DNA with various effector/target (E/T) ratios (1:1, 3:1, 9:1, 27:1) using an E7-specific T cell line. As shown in FIG. 6, 293 $D^bK^b$ cells transfected with CRT/E7 DNA induced significantly higher percentages of specific lysis at the 9:1 (20.5+1.0% versus 10.43+0.9%, P<0.001) and 27:1 (47.1+5.5% versus 15.1+3.0%, P<0.001) E/T ratios compared to mice vaccinated with only wild-type E7 DNA vaccine. These results indicated that cells transfected with the chimeric CRT/E7 constructs of the invention were capable of presenting E7 antigen via "direct priming" through the MHC class I pathway in a more efficient manner than cells transfected with wild-type E7 DNA.

Figure 7:
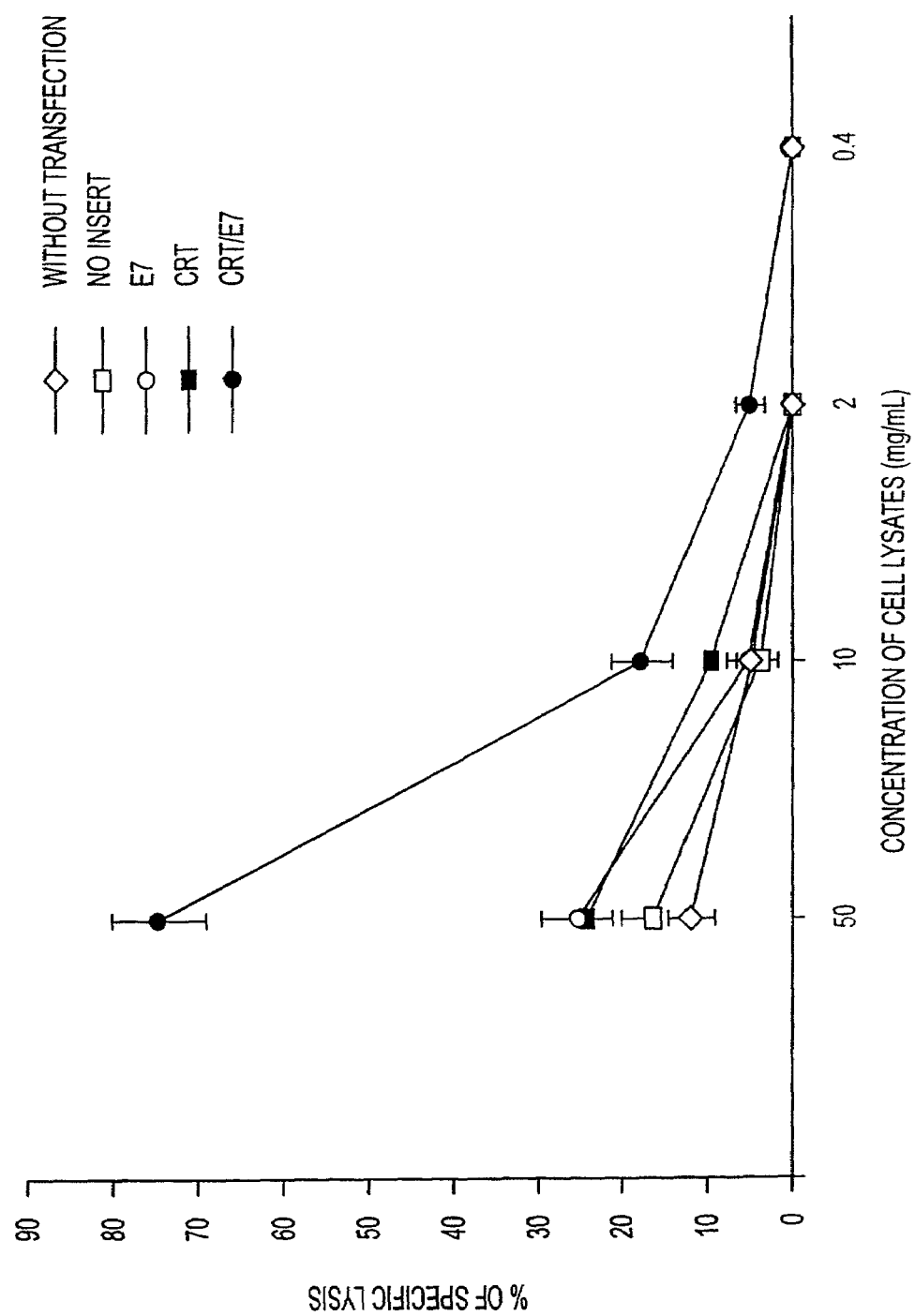
FIG. 7 shows a schematic summary of data from a cross-priming experiment to characterize the MHC class I presentation of E7 dendritic cells pulsed with cell lysates of 293 $D^bK^b$ cells transfected with various naked DNA constructs. E7-specific CD8+ T cells served as effector cells; bone marrow-derived DCs were pulsed with a serial dilution of lysates of transfected 293 $D^bK^b$ cells (50 mg/ml, 10 mg/ml, 2 mg/ml and 0.4 mg/ml); DCs were used as target cells while E7-specific CD8+ T cells served as effector cells as discussed in Example 1, below.

Enhanced Presentation of E7 Through the MHC Class I Pathway in Dendritic Cells Pulsed With Chimeric CRT/E7 Protein: Another potential mechanism for enhanced E7-specific CD8+ T cell immune responses in vivo is the presentation of E7 through the MHC class I pathway by antigen-presenting cells via uptake of lysed cells expressing various DNA constructs, also called "cross-priming". A cross priming experiment was performed to characterize the MHC class I presentation of E7 dendritic cells pulsed with cell lysates of 293 $D^bK^b$ cells transfected with empty plasmid, calreticulin, E7, or CRT/E7 DNA. E7-specific CD8+ T cells served as effector cells. As mentioned previously, 293 $D^bK^b$ cells have been shown to have stable transfection efficiency and similar E7 expression among cells transfected with different E7-containing DNA constructs. Lysates of transfected 293 $D^bK^b$ cells were obtained from cycles of freeze-thaw. Bone marrow-derived DCs were pulsed with a serial dilution of lysates of transfected 293 $D^bK^b$ cells (50 Tg/ml, 10 Tg/ml, 2 Tg/ml and 0.4 Tg/ml). DCs were used as target cells while E7-specific CD8+ T cells served as effector cells. CTL assays were performed with a fixed E/T ratio (9/1). As shown in FIG. 7, DCs pulsed with lysates of 293 $D^bK^b$ cells transfected with CRT/E7 DNA induced significantly higher percentages of specific lysis compared to DCs pulsed with lysates of 293 $D^bK^b$ cells transfected with the other DNA constructs and naive DCs (P<0.001). Theses results revealed that dendritic cells pulsed with CRT/E7 fusion protein (present in the cell lysate of transfected 293 $D^bK^b$ cells) are capable of presenting E7 antigen through the MHC class I pathway in a more efficient manner than dendritic cells pulsed with lysates of 293 $D^bK^b$ cells transfected only with wild-type E7 protein-encoding constructs. This data demonstrates that the fusion of CRT to E7, i.e., expression of the E7 polypeptide as a fusion protein with calreticulin, enhances E7-specific CD8+ T cell immune responses via both direct and cross priming effects.

Figure 8:
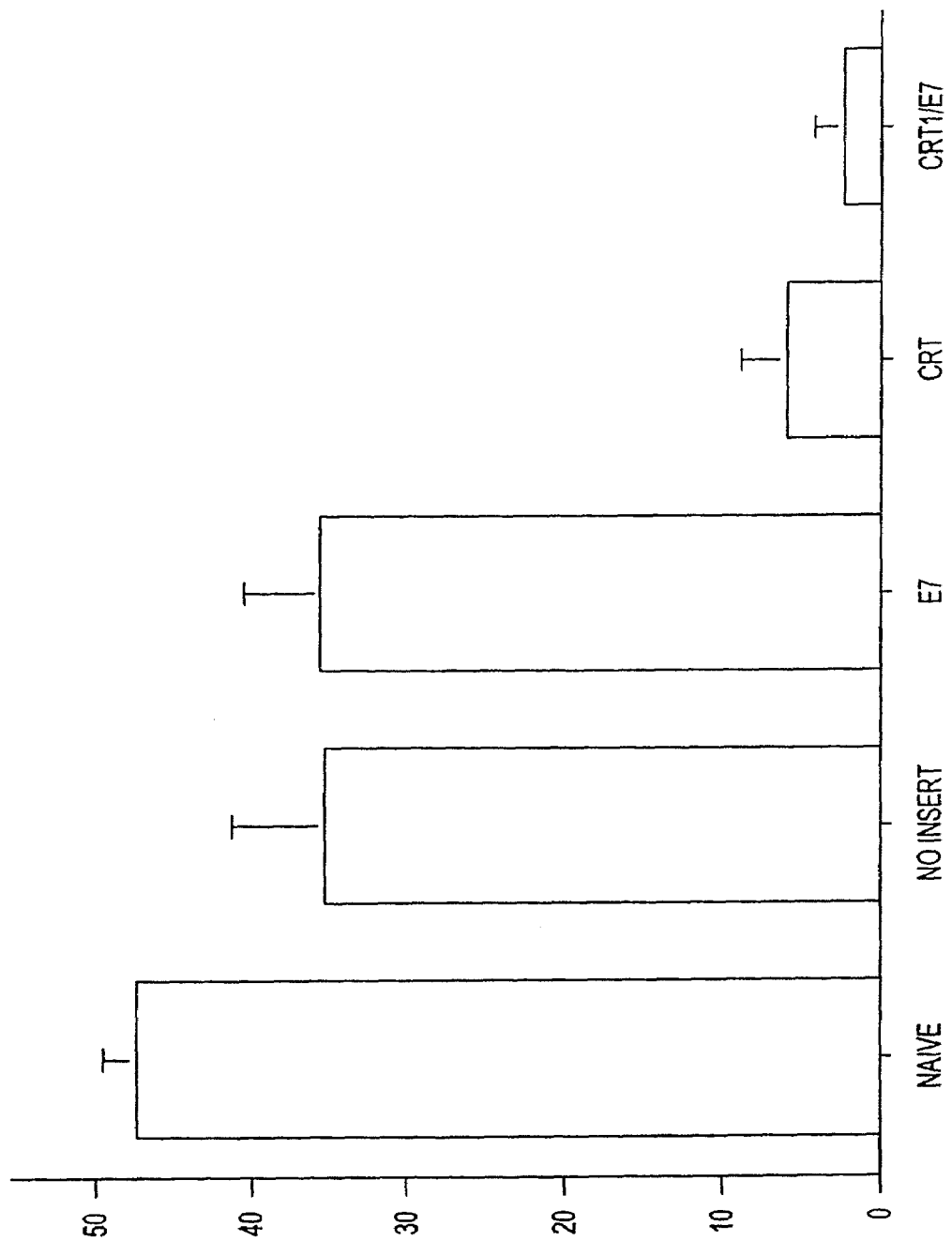
FIG. 8 shows a schematic summary of data from an experiment designed to evaluate the role of CRT/E7 fusion polypeptides as compared to E7 or CRT polypeptide alone in the treatment of TC-1 tumor metastases in the lungs without any immune effector cells (i.e., in nude mice); nude mice were first challenged with tumor cells and two days after challenged with TC-1 tumor cells; thereafter mice were vaccinated with various naked DNA constructs. On day 9 and day 16, these mice were boosted with the same regimen as the first vaccination. The mice were sacrificed on day 21 and the pulmonary nodules of each mouse were evaluated and counted, as discussed in Example 1, below.

Treatment with CRT or Chimeric CRT/E7 DNA Vaccines Eradicates Established Tumors in the Lungs of Nude Mice: As discussed above, mice treated with wild-type CRT DNA displayed a lower mean number of lung nodules than mice receiving only wild-type E7 DNA or no vaccination (one-way ANOVA, P<0.001). Since mice vaccinated with CRT did not induce E7-specific T cell immune responses (see FIG. 2), the therapeutic effects (decrease in numbers of metastatic lung nodules) observed when constructs expressing CRT alone are administered may not be related to the anti-tumor immune responses (i.e., increase in antigen specific CTLs). To evaluate the role of CRT/E7 fusion polypeptides as compared to E7 or CRT polypeptide alone in the treatment of TC-1 tumor metastases in the lungs without any immune effector cells, nude (BALB/c nu/nu) mice (animals lacking both T helper and killer (CTL) lymphocytes and unable to induce either a humoral or a cellular immune response) were first challenged with $1\times10^4$ TC-1 tumor cells per mouse via intravenous tail vein injection, as discussed above. Two days after challenge with TC-1 tumor cells, mice were given 16 Tg of CRT-encoding, E7-encoding or CRT/E7-encoding DNA, or empty plasmid without insert, via gene gun. On day 9 and day 16, these mice were boosted with the same regimen as the first vaccination. The mice were sacrificed on day 21. The pulmonary nodules of each mouse were evaluated and counted. As shown in FIG. 8, nude mice treated with constructs expressing CRT alone or the CRT/E7 fusion protein revealed a lower mean number of pulmonary nodules (6.0+2.8 for CRT, 2.5+0.7 for CRT/E7) compared to mice vaccinated with only wild-type E7 DNA (36.0+2.8), vector only (35.5+12.0) or naive group (47.5+2.1) (one-way ANOVA, P<0.001). These data indicated that the antitumor effects induced by CRT or CRT/E7 DNA vaccines were independent of anti-tumor immune responses.

Treatment ent with CRT or Chimeric CRT/E7 DNA Vaccines Significantly Reduced the Microvessel Density of the Tumors in the Lungs of Nude Mice: To determine whether this anti-tumor effect of CRT or CRT/E7 DNA in the absence of immune effectors is via an anti-angiogenic pathway, microvessel density (MVD) in the pulmonary tumors of nude mice treated with various DNA vaccines was measured. The endothelial cells were stained with anti-CD31 antibody as described above. All measurements were performed by a single pathologist without knowing any treatment data before counting. Nude mice (lacking a functional immune system) vaccinated with either the CRT or CRT/E7 DNA vaccines revealed much less MVD in the pulmonary tumors than nude mice treated with wild-type E7 or the control vector group (one-way ANOVA, P<0.001). These data indicated that mice treated with either CRT-expressing or CRT/E7 fusion protein-expressing vaccines could lead to anti-angiogenesis effects in the tumors.

EXAMPLE 2

Self-replicating RNA Viruses Induce Enhanced Antigen-specific CTL Responses

In one embodiment, the invention provides a self-replicating RNA replicon that can express a chimeric protein of the invention: a protein that comprises a first polypeptide domain comprising an endoplasmic reticulum (ER) chaperone polypeptide and a second polypeptide domain comprising at least one antigenic peptide. The following example describes studies which demonstrate that, using the methods of the invention, these constructs are effective for enhancing antigen-specific cytotoxic T lymphocyte (CTL) responses in vivo. As a model system, a fusion protein comprising HPV-16 E7 and *Mycobacterium tuberculosis* HSP70 was expressed in vivo in a Sindbis virus self-replicating RNA vector, SINrep5. The potency of antigen-specific immunity induced by this vector was determined. These results also demonstrate that fusion proteins comprising an ER chaperone polypeptide and an antigenic peptide expressed in vivo in a Sindbis virus self-replicating RNA vector are effective for enhancing antigen-specific CTL responses in vivo.

These experiments demonstrated that an RNA replicon vaccine containing E7/HSP70 fusion genes induced significantly higher E7-specific T cell-mediated immune responses than vaccines containing the wild type E7 gene in vaccinated mice. Furthermore, in vitro studies demonstrated that E7 antigen from E7/HSP70 RNA replicon-transfected apoptotic cells can be taken up by bone marrow-derived dendritic cells and presented more efficiently through the MHC class I pathway than wild-type E7 RNA replicon-transfected apoptotic cells. More importantly, the fusion of HSP70 to E7 converted a less effective vaccine into one with significant potency against E7-expressing tumors. This antitumor effect was dependent on NK cells and $CD8^+$ T cells. These results indicated that fusion of HSP70 to an antigen gene greatly enhanced the potency of self-replicating RNA vaccines. These results demonstrated that a Sindbis RNA vaccine linking E7 with HSP70 dramatically increased expansion and activation of E7-specific CD8+ T cells and NK cells, completely bypassing the CD4 arm and resulting in potent anti-tumor immunity against E7-expressing tumors.

The mechanism of Sindbis RNA vaccine to promote the anti-tumor effect was further investigated. It was found that the Sindbis E7/HSP70 RNA vaccine could induce apoptotic death of host cells and promote dendritic cells to phagocytose these cells, dramatically increasing the expansion and activation of E7-specific CD8+ T cells. This enhanced CD8 response resulted in potent anti-tumor immunity against an E7-expressing tumor cell line.

HPV-16 E7 was chosen as a model antigen for vaccine development because HPVs particularly HPV-16, are associated with most cervical cancers, as discussed above.

Plasmid DNA Constructs and Preparation: The vectors pcDNA3-HSP70, pcDNA3-E7, and pcDNA3-E7/HSP70 were made as described by Chen (2000) supra. The Sindbis virus RNA replicon vector, SINrep5 has been described by, Bredenbeek, supra. Vectors SINrep5-HSP70, SINrep5-E7, and SINrep5-E7/HSP70 were made by isolating DNA fragments encoding *Mycobacterium tuberculosis* HSP70, HPV-16 E7 and chimeric E7/HSP70 by cutting pcDNA3-HSP70, pcDNA3-E7, and pcDNA3-E7/HSP70, respectively, with XbaI and PmeI restriction enzymes. Digested products were isolated using gels. These isolated DNA fragments were further cloned into the corresponding XabI and Pml I sites of the SINrep5 vector to induce SINrep5-HSP70, SINrep5-E7, and SINrep5-E7/HSP70 constructs. The accuracy of these constructs was confirmed by DNA sequencing.

In Vitro RNA Preparation: The generation of RNA transcripts from SINrep5-HSP70, SINrep5-E7, SINrep5-E7/HSP70 and SINrep5 was performed using the protocol described by MandI (1998) Nature Med 4:1438-1440. SpeI was used to linearize DNA templates for the synthesis of RNA replicons from SINrep5-HSP70, SINrep5-E7, SINrep5-E7/HSP70 and SINrep5. RNA vaccines were transcribed in vitro and capped using SP6 RNA polymerase and capping analogue from a standard in vitro transcription kit (Life Technologies, Rockville, Md.) according to vendor's manual. After synthesis, DNA was removed by digestion with DNase I. Synthesized RNA was quantified and analyzed using denaturing formaldehyde agarose gels (Mandl (1998) supra). The purified RNA was divided into aliquots to be used for vaccination in animals and for transfection of a BHK21 cell line. The protein expression of the transcripts was assessed by transfection of the RNA into BHK21 cells using electroporation.

Cell Lines: Baby hamster kidney (BHK21) cells were obtained from the ATCC (Rockville, Md.) and grown in Glasgow MEM supplemented with 5% FDS, 10% tryptose phosphate broth, 2 mM glutamine, and antibiotics. Cells were kept at 37° C. in a humidified 5% CO2 atmosphere and were passaged every 2 days. The production and maintenance of TC-1 cells was done as described by Lin (1996) Cancer Res. 56:21-26. On the day of tumor challenge, TC-1 cells were harvested by trypsinization, washed twice with 1× Hanks buffered salt solution (HBSS), and finally resuspended in 1×HBSS to the designated concentration for injection.

ELISA for E7 Protein Expression of SINrep5 RNA vaccines: The expression of E7 protein from SINrep5-E7 and SINrep5-E7/HSP70 RNA was determined by an indirect ELISA method. The quantity of E7 protein was determined using cell lysates from SIN5rep-E7 or -E7/HSP70 transfected BHK21 cells. Briefly, ten million BHK21 cells were transfected with the 4 µg SINrep5, SINrep5-E7, SINrep5-HSP70 or SINrep5-E7/HSP70 RNA transcripts respectively via electroporation as described by Liljestrom (1991) J. Virol. 65:4107-4113. The transfected BHK21 cells were collected 16-20 hrs after electroporation. A 96-microwell plate was coated BHK 21 cell lysates that were transfected with various SINrep5 RNAs in a final volume of 100 µl, and were incubated at 4° C. overnight. The bacteria-derived HPV-16 E7 proteins were used as a positive control. The wells were then blocked with PBS containing 20% fetal bovine serum. Diluted anti-E7 Ab (Zymed, San Francisco, Calif.) were added to the ELISA wells, and incubated on 37° C. for 2 hr. After washing with PBS containing 0.05% Tween-20, the plate was incubated with 1/2000 dilution of a peroxidase-conjugated rabbit anti-mouse IgG antibody (Zymed, San Francisco, Calif.) at room temperature (RT) for one hour. The plate was washed, developed with 1-Step™ Turbo TMB-ELISA (Pierce, Rockford, Ill.), and stopped with 1M $H_2SO_4$. The ELISA plate was read with a standard ELISA reader at 450 nm. The quantity of E7 protein of the cell lysates was then calculated and determined by comparing with the standardized E7 protein.

Mice: 6 to 8-week-old female C57BL/6 mice from the National Cancer Institute (Frederick, Md.) were purchased and kept in the oncology animal facility of the Johns Hopkins Hospital (Baltimore, Md.). All animal procedures were performed according to approved protocols and in accordance with recommendations for the proper use and care of laboratory animals.

RNA Vaccination: All SINrep5 RNA vaccines were generated using in vitro transcription as described above. RNA concentration was determined by optical density measured at 260 rm. The integrity and quantity of RNA transcripts were further checked using denaturing gel electrophoresis. Mice were vaccinated intramuscularly with $10_g$ of various SINrep5 RNAs in the right hind leg except for SINrep5-E7/HSP70, which was administered in 0.1, 1, and 10 µg quantities.

ELISA for E7 Antibodies: Anti-HPV 16 E7 antibodies in the sera were determined by a direct ELISA as described by Wu (1995) Proc. Natl. Acad. Sci. USA 92:11671-1165. A 96-microwell plate was coated with 100 µl 5 µg/ml bacteria-derived HPV-16 E7 proteins and incubated at 4° C. overnight. The wells were then blocked with PBS containing 20% fetal bovine serum. Sera were prepared from mice on day 14 post-immunization, serially diluted in PBS, added to the ELISA wells, and incubated on 37° C. for 2 hr. After washing with PBS containing 0.05% Tween-20, the plate was incubated with 1/2000 dilution of a peroxidase-conjugated rabbit anti-mouse IgG antibody (Zymed, San Francisco, Calif.) at RT for one hour. The plate was washed, developed with 1-Step™ Turbo TMB-ELISA (Pierce, Rockford, Ill.), and stopped with 1M $H_2SO_4$. The ELISA plate was read with a standard ELISA reader at 450 nm.

Enzyme-Linked Immunoabsorbent Assay (ELISA) for INF-γ: Splenocytes were harvested 2 weeks after vaccination and cultured with the E7 peptide (aa 49-57) containing MHC class I epitope (Feltkamp (1993) Eur. J. Immunol. 23:2242-2249) or the E7 peptide (aa 30-67) containing MHC class II peptide (Tindle, supra), in a total volume of 2 ml of RPMI 1640, supplemented with 10% (vol/vol) fetal bovine serum, 50 units/ml penicillin and streptomycin, 2 mM L-glutamine, 1 mM sodium pyruvate, 2 mM nonessential amino acids in a 24-well tissue culture plate for 6 days. The supernatants were harvested and assayed for the presence of IFN-γ using ELISA kits (Endogen, Woburn, Mass.) according to the manufacturer's protocol.

Cytotoxic T Lymphocyte (CTL) Assays: CTL assays were performed in 96-well round-bottom plates as described by Corr (1999) J. Immunol. 163:4721-4727. Cytolysis was determined by quantitative measurements of lactate dehydrogenase (LDH) (Corr (1999) supra). Splenocytes were harvested 2 weeks after RNA vaccination and cultured with the E7 peptide (aa 49-57) in a total volume of 2 ml of RPMI 1640, supplemented with 10% (vol/vol) fetal bovine serum, 50 units/ml penicillin/streptomycin, 2 mM L-glutamine, 1 mM sodium pyruvate, 2 mM nonessential amino acids in a 24-well tissue culture plate for 6 days as effector cells. TC-1 tumor cells were used as target cells. The TC-1 cells mixed with splenocytes at various effector/target (E/T) ratios. After 5 hr incubation at 37° C., 50 µl of the cultured media were collected to assess the amount of LDH in the cultured media according to the manufacturer's protocol of the CytoTox™ assay kits (Promega, Madison, Wis.). The percentage of lysis was calculated from the following equation: $100\times(A-B)/(C-D)$, where A is the reading of experimental-effector signal value, B is the effector spontaneous background signal value, C is maximum signal value from target cells, D is the target spontaneous background signal value.

Intracytoplasmic Cytokine Staining and Flow Cytometry Analysis: Splenocytes from naïve or vaccinated groups of mice were incubated with the E7 peptide (aa 30-67) that contains MHC class II peptide (Tindle (1999) supra) for detecting E7-specific $CD4^+$ T helper cell precursors. The E7 peptide was added at a concentration of 10 µg/ml for 20 hours. Golgistop™ (PharMingen, San Diego, Calif.) was added 6 hours before harvesting the cells from the culture. Cells were then washed once in FACScan™ buffer and stained with phycoerythrin (PE)-conjugated monoclonal rat anti-mouse CD4 antibody (PharMingen, San Diego, Calif.). Cells were subjected to intracellular cytokine staining using the Cytofix/Cytoperm™ kit according to the manufacturer's instructions (PharMingen). FITC-conjugated anti-IFN-γ antibody and the immunoglobulin isotype control antibody (rat IgG1) were all purchased from PharMingen. Analysis was done on a Becton Dickinson FACScan™ with CELLQuest™ software (Becton Dickinson Immunocytometry System, Mountain View, Calif.).

In Vivo Tumor Protection Experiments: For the tumor protection experiment, mice (5 per group) were immunized intramuscularly (IM) with different doses of SINrep5-HSP70, SINrep5-E7, SINrep5-E7/HSP70, and empty SINrep5 RNA vaccines. 14 days after immunization, mice were injected intravenously (IV) with $1\times10^4$ cells/mouse TC-1 tumor cells in the tail vein. Three weeks later, mice were euthanized. The lung weight and number of pulmonary nodules in each mouse was evaluated and counted by experimenters in a blinded fashion.

In Vivo Antibody Depletion Experiments: The procedure for ill vivo antibody depletion has been described previously by, e.g., Lin (1996) supra; Wu (1995) J. Exp. Med. 182: 1415-1421. In brief, mice were vaccinated with 1 µg self-replicating SINrep5-E7/HSP70 RNA intramuscularly and challenged with $1\times10^4$ cells/mouse TC-1 tumor cells via tail vein injection. Depletions were started one week prior to tumor challenge. MAb GK1.5 (Dialynas (1983) J. Immunol. 131:2445) was used for CD4 depletion, MAb 2.43 Sarmiento (1980) J. Immunol. 125:2665) was used for CD8 depletion, and MAb PK136 (Koo (1986) J. Immunol. 137: 3742) was used for NK1.1 depletion. Flow cytometry analysis revealed that >95% of the appropriate lymphocytes subset were depleted with a normal level of other subsets. Depletion was terminated on day 21 after tumor challenge.

Cell Surface Marker Staining and Flow Cytometry Analysis: Splenocytes removed from naïve or vaccinated groups of mice were immediately treated with cell surface marker staining as described by Ji (1999) Human Gene Therapy 10:2727-2740. Cells were then washed once in FACS-CAN™ buffer and stained with PE-conjugated monoclonal rat anti-mouse NK1.1 antibody and FITC-conjugated monoclonal rat anti-mouse CD3 antibody (Pharmingen, San Diego, Calif.). The population of NK cells was stained with anti-NK1.1 antibody and not stained with anti-CD3 antibody. The percentages of NK cells in mice immunized with various self-replicating RNA vaccines was analyzed using flow cytometry.

Generation and Culture of Dendritic Cells (DCs) from Bone Marrow. DCs were generated by culture of bone marrow cells in the presence of GM-CSF as described by Lu (2000) J. Exp. Med. 191:541-550. Briefly, bone marrow was collected from the tibias of mice. Erythrocytes were lysed, and the remaining cells were passed through a nylon mesh to remove small pieces of bone and debris. The cells were collected and $1\times10^6$ cells/ml were placed in 24-well plates in RMPI 1640, supplemented with 5% FCS, 2 mM β-mercaptoethanol, 1% non-essential amino acids, 100 U/ml penicillin and 100 µg/ml streptomycin (Life Technologies, Rockville, Md.), and 100 U/ml GM-CSF (PharMingen, San Diego, Calif.). Two-thirds of the medium was replaced every 2 days, and non-adherent cells were harvested on day 7. The collected cells were characterized by flow cytometry analysis (FACS) for DC markers.

Generation of E7-Specific CD8+ T Cell Lines: Generation of E7-specfic CD8+ cell lines was done by immunizing female C57BL/6 (H-2b) mice by intraperitoneal (IP) injection of Sig/E7/LAMP-1 vaccinia. Splenocytes were harvested on day 8. For initial in vitro stimulation, splenocytes were pulsed with IL-2 at a concentration of 20 U/ml and 1 µM E7 peptide (amino acids 49-57) for 6 days. Propagation of the E7-specific CTL cell line was performed in 24-well plates by mixing (2 ml/well) $1\times10^6$ splenocytes containing E7-specific CTLs with $3\times10^6$ irradiated splenocytes and pulsing them with IL-2 at a concentration of 20 U/ml and 1 µM E7 peptide (amino acids 49-57). This procedure was repeated every 6 days. The specificity of the E7 CTL line was characterized by the CTL assay. Flow cytometry was performed to demonstrate the expression of the CD8 marker.

In Vitro Cell Death Analysis: Ten million BHK21 cells were transfected with 4 µg SINrep5, SINrep5-E7, SINrep5-HSP70 or SINrep5-E7/HSP70 RNA transcripts as mentioned earlier. Native BHK21 cells or BHK21 cells that were electroporated without SINrep5 RNA were used as controls. BHK21 cells were collected and assessed every 24 hr, until hour 72. The percentages of apoptotic and necrotic BHK21 cells were analyzed using annexin V apoptosis detection kits (PharMingen, San Diego, Calif.) according to the manufacturer's protocol, followed by flow cytometry analysis.

CTL Assay Using DCs Pulsed with Apoptotis Cells as Target Cells: CTL assays using DCs pulsed with apoptosis cells as target cells were performed using a protocol similar to that described by Albert (1998) Nature 392:86-89; Albert (1998) J. Exp. Med. 188:1359-1368; with modification. Briefly, 10 million BHK21 cells were transfected with 4 µg of various self-replicating SINrep5 RNAs via electroporation. BHK21 cells were collected 16-20 hr after electroporation. The levels of E7 protein expression in BHK21 cells transfected with SINrep5-E7, or SINrep5-E7/HSP70 RNA transcripts were similar, as determined by ELISA. $3\times10^5$ transfected BHK21 cells were then co-incubated with $1\times10^5$ of bone marrow-derived DCs at 37° C. for 48 hr. These prepared DCs were then used as target cells and the Db-restricted E7-specific CD8+ T cells were used as the effector cells. CTL assays were performed with effector cells and targets cells ($1\times10^4$ per well) mixed together at various ratios (1:1, 3:1, 9:1, and 27:1) in a final volume of 200 µl. After 5 h incubation at 37° C., 50 µl of the cultured media were collected to assess the amount of LDH in the cultured media as described above. DCs co-incubated with untransfected BHK21 cells, transfected BHK21 cells alone, untreated DCs alone, and CD8+ T cell line alone were included as negative controls.

Construction and Characterization of Self-replicating RNA Constructs: Generation of plasmid DNA constructs and subsequent preparation of self-replicating SINrep5-RNA constructs was performed as described above. The SINrep5 vector contains the genes encoding Sindbis virus RNA replicase and the SP6 promoter (Bredenbeek (1993) supra). The schematic diagram of SINrep5, SINrep5-HSP70, SINrep5-E7, SINrep5-E7/HSP70 DNA constructs was shown in FIG. 9A. In addition, the schematic diagram of RNA transcript derived from these DNA constructs using SP6 RNA polymerase was shown in FIG. 9B. A methylated $M^7G$ "cap" is located at the 5' end of the mRNA, followed by a sequence responsible for the self-replication (replicase), the gene of interest (i.e., an MHC class I peptide epitope, an E7, an HSP70, an E7/HSP70, or the like), and a polyadenylated tail (AAAA). An ELISA was performed to demonstrate the expression of E7 protein by BHK21 cells transfected with the various self-replicating RNA constructs. SINrep5-E7 and SINrep5-E7/HSP70 expressed similar amounts of E7 protein.

Vaccination with Self-replicating SINrep5-E7/HSP70 RNA Enhances an E7-Specific Cytotoxic Immune Response: CD8+ T lymphocytes are one of the most crucial effectors for inducing anti-tumor immunity. To determine the quantity of E7-specific CD8+ T cell responses induced by the SINrep5-E7/HSP70 RNA vaccine, CTL assays were used. Mice were immunized with various SINrep5 self-replicating RNA vaccines via intramuscular injection. Splenocytes and serum samples were collected after 14 days. To perform the cytotoxicity assay, splenocytes from the various self-replicating SINrep5 RNA vaccines were cultured with E7 peptide (aa 49-57) containing MHC class I epitope for 6 days as effector cells. TC-1 tumor cells were as target cells.

The TC-1 cells mixed with splenocytes at various E/T (effector/target ratio). Cytolysis was determined by quantitative measurements of LDH. CTL assays shown here are from one representative experiment of two performed.

The self-replicating RNA E7/HSP70 vaccine induced significantly higher percentage of specific lysis as compared with the other RNA vaccines (*: P<0.001, one-way ANOVA). The self-replicating SINrep5-E7/HSP70 induced a significantly higher percentage of specific lysis compared to mice vaccinated with the other SINrep5 RNA vaccines (P<0.001, one-way ANOVA). The ability of SINrep5-E7/HSP70 RNA to induce specific lysis was found to be approximately 4 times that of self-replicating SINrep5-E7 RNA (32.7% versus 8.8%, E/T ratio 45/1, P<0.001).

Vaccination with Self-replicating SINrep5-E7/HSP70 RNA Enhances E7-specific $CD8^+$ T cells to Secrete High Levels of INF-$\gamma$: To determine the extent of the immunological response of E7-specific $CD8^+$ T cells induced by self-replicating SINrep5-E7/HSP70 RNA, an ELISA was used to detect the concentration of INF-$\gamma$ in the supernatant of cultured splenocytes. Mice were immunized with various self-replicating RNA vaccines via intramuscular injection. Splenocytes and serum samples were collected after 14 days. Splenocytes from the various self-replicating RNA vaccines were cultured in vitro with E7 peptide (aa 49-57) containing the MHC class I epitope (or without any peptide) for 6 days. As a negative control, an ELISA was also performed without peptide. Supernatants in the culture medium were collected to detect the INF-$\gamma$ concentration using an ELISA.

Splenocytes from the self-replicating E7/HSP70 RNA group stimulated with E7 peptide (aa 49-57) secreted the highest concentration of INF-$\gamma$ compared to the other RNA vaccines (P<0.001, one-way ANOVA). These results also indicated that fusion of HSP70 to E7 significantly enhances INF-$\gamma$-secreting E7-specific $CD8^+$ T cell activity. Thus, the $CD8^+$ T cells could be induced by the MHC class I epitope of E7. Note: the splenocytes from the self-replicating E7/HSP70 RNA group stimulated with E7 peptide (aa 49-57) secreted the highest concentration of INF-$\gamma$ compared to the other RNA vaccines (*: P<0.001, one-way ANOVA).

Vaccination with Self-replicating SINrep5-E7/HSP70 RNA Does Not Induce Significant E7-Specific $CD4^+$ T Cell-Mediated Immune Responses: To examine the generation of E7-specific $CD4^+$ T precursor cells and cytokine profiles by each of these RNA vaccines, we performed double staining for CD4 surface marker and intracellular IFN-$\gamma$ on splenocytes obtained from immunized mice, followed by flow cytometry analysis. The splenocytes were cultured in vitro with E7 peptide (aa 30-67) overnight and stained for both CD4 and intracellular IFN-$\gamma$. The E7 peptide (aa 30-67) contains a major T helper epitope in the E7 open reading frame protein of HPV-16 (Tindle (1991) supra). The percentage of IFN-$\gamma$-secreting $CD4^+$ T cells was analyzed using flow cytometry.

Mice vaccinated with SINrep5-E7/HSP70 RNA induced a similar number of $CD4^+$ IFN-$\gamma^+$ double positive cells compared to mice vaccinated with SINrep5-E7 RNA ($15/3 \times 10^5$ splenocytes versus $12/3 \times 10^5$ splenocytes, p>0.05) or other RNA groups. There was no significant difference in the number of E7-specific $CD4^+$ IFN-$\gamma^+$ cells observed using flow cytometry staining among naïve mice or mice vaccinated with empty plasmid, E7, HSP70, or E7/HSP70 RNA. Splenocytes from Sig/E7/LAMP-1 DNA vaccinated mice (Ji (1999) supra) were used as positive controls for intracellular IFN-$\gamma$ staining for this study.

The quantity of anti-HPV 16 E7 antibodies in the sera of the vaccinated mice was determined using a direct enzyme-linked immunoabsorbent assay (ELISA) 2 weeks after vaccination at various dilutions (1:100, 1:500, 1:1000). SINrep5-E7/HSP70 did not induce higher titers of E7-specific antibodies in the sera of vaccinated mice compared to that induced by other RNA vaccine constructs.

Vaccination with Self-Replicating SINrep5-E7/HSP70 RNA Protects Alice Against the Growth of TC-1 Tumors: To determine whether vaccination with the self-replicating SINrep5-E7/HSP70 RNA protected mice against E7-expressing tumors, an in vivo tumor protection experiment was performed using different doses of SINrep5-E7/HSP70 RNA administered intramuscularly in the right hind leg. Mice were similarly vaccinated with 10 μg self-replicating SINrep5, SINrep5-HSP70, and SINrep5-E7 RNA. Different doses of self-replicating SINrep5-E7/HSP70 RNA including 0.1 μg, 1 μg and 10 μg were also injected into mice. One week after vaccination, mice were challenged with TC-1 tumor cells via intravenous tail vein injection at a dose of $2 \times 10^4$ cells/mouse. Mice were monitored twice a week and sacrificed at day 21 after tumor challenge. The pulmonary nodules were assessed 21 days after tumor challenge. Lungs were dissected from the mice 35 days after vaccination with empty SINrep5 (10 μg), SINrep5-HSP70 (10 μg), SINrep5-E7 (10 μg), and SINrep5-E7/HSP70 RNA (0.1 μg, 1 μg, or 10 μg) The mean number of lung foci was used as a measurement of the effectiveness of the various self-replicating RNA vaccines at controlling HPV-16 E7-expressing tumor growth.

The mean pulmonary nodules of mice vaccinated with the self-replicating E7/HSP70 RNA vaccines (0.1 μg, 1 μg, and 10 μg) were much less compared to mice vaccinated with the other RNA vaccines (P<0.001, one-way ANOVA). These results demonstrated that self-replicating RNA SINrep5-E7/HSP70 vaccines protect mice from intravenous tumor challenge even at the low dosage of 0.1 μg while mice vaccinated with RNA from 10 μg SINrep5 without insert, 10 μg SINrep5-E7, or 10 μg SINrep5-HSP70 developed numerous lung nodules from TC-1 tumor challenge.

$CD8^+$ T Cells and NK cells Are Important for the Antitumor Effect Induced by Vaccination with SINrep5-E7/HSP70 RNA Vaccines: To determine the types of lymphocytes that are important for protection against E7-expressing tumor cells, in vivo antibody depletion (of $CD8^+$ T cells and NK cells) experiments were performed (the percentage of NK cells from the splenocytes of mice immunized with self-replicating RNA vaccines were higher than that without immunization and there was no significant difference between the percentage of NK cells among the various self-replicating RNA vaccines). The antibody depletion was started one week before tumor challenge and terminated on day 21 after tumor challenge.

The mean pulmonary nodules from mice depleted of $CD8^+$ T cells and NK1.1 cells were significantly higher than those of non-depleted group. Furthermore, depletion of NK1.1 cells resulted in a higher mean number of tumor lung nodules than CD8+ depleted mice.

In comparison, the mean pulmonary nodules from mice depleted of $CD4^+$ T cells resembled results obtained from non-depleted mice, indicating that $CD4^+$ T cells were not critical in generating this effect. These results suggest that $CD8^+$ T cells are essential for the antigen-specific anti-tumor immunity induced by SINrep5-E7/HSP70 RNA vaccine and that NK cells, while not limited to the E7/HSP70 RNA vaccine, play an important role as well.

It was also investigated whether the NK cell effect was limited to the E7/HSP70 vaccines or if it was the result of the vector used. Flow cytometry analysis of CD3(−), NK1.1(+) cells revealed that their presence was markedly increased in all constructs (E7/HSP70, E7, HSP70, and control plasmid) relative to naïve mice, indicating that NK cells were important effectors of the anti-tumor effect that are not limited to the E7/HSP70 vaccines.

Self-Replicating RNA Vaccines Induce Apoptosis: RNA transcribed in vitro from various plasmid SINrep5 RNA vaccines were transfected into BHK21 cells via electroporation. Electroporated BHK 21 cells without RNA and untreated BHK21 cells were used as controls.

The percentages of apoptotic and necrotic BHK21 cells were stained by annexin V-FITC and propidium iodide (PI) followed by flow cytometry analysis.

The percentages of apoptotic BIM 1 cells revealed statistical declines when transfected with SINrep5 RNA vaccines, 24 hr to 72 hr after (representative with SIN5-E7/HSP70 70.3±3.6% for 24 hr, 49.3±4.2% for 48 hr 18.0±3.1% for 72 hr, $P<0.001$, one-way ANOVA). BHK21 cells transfected with SINrep5 RNA vaccines induced higher percentages after 24, 48 or 72 hours later compared to the other two control groups. No statistical differences could be found in the apoptotic percentages of various SINrep5 RNA vaccines.

Enhanced Presentation of E7 through the MHC Class I Pathway in Dendritic Cells Pulsed With Cells Transfected with SINrep5-E7/HSP70 RNA: A potential mechanism for the enhanced E7-specific $CD8^+$ T cell immune responses in vivo is the presentation of E7 through the MHC class I pathway by uptake of apoptotic bodies from cells expressing various E7 constructs, also called "cross-priming". A cross priming experiment was performed to characterize the MHC class I presentation of E7 in dendritic cells pulsed with apoptotic bodies from BHK21 cells transfected with various self-replicating RNA. As mentioned previously, BHK21 cells have been shown to have stable high transfection efficiency and similar E7 expression among cells transfected with different E7-containing self-replicating RNA. Transfected BHK21 cells were co-incubated with bone marrow-derived DCs. DCs were used as target cells while E7-specific $CD8^+$ T cells served as effector cells. CTL assays with various E/T ratios were performed.

DC target cells co-incubated with BHK21 cells transfected with SINrep5-E7/HSP70 RNA induced significantly higher percentages of specific lysis compared to DCs co-incubated with BHK21 cells transfected with SINrep5-E7 RNA ($P<0.001$). These results suggested that dendritic cells pulsed with apoptotic bodies containing E7/HSP70 fusion protein presented E7 antigen through the MHC class I pathway more efficiently than dendritic cells pulsed with apoptotic bodies containing wild-type E7 protein. Thus, the fusion of HSP70 to E7 enhanced E7-specific $CD8^+$ T cell immune responses; and, while the invention is not limited by any particular mechanism, the enhancement was likely via "cross priming."

A number of embodiments of the invention have been described. Nevertheless, it will be understood that various modifications may be made without departing from the spirit and scope of the invention. Accordingly, other embodiments are within the scope of the following claims.

What is claimed is:

1. A nucleic acid molecule encoding a fusion polypeptide useful as an immunogenic or vaccine composition, which molecule comprises:
   (a) a first nucleic acid sequence encoding a first polypeptide that is a calreticulin (CRT) polypeptide or an active CRT fragment which fragment corresponds to:
      (i) an N-terminal fragment of human CRT, the amino acid sequence of which is residues 1-180 of SEQ ID NO:2; or
      (ii) a C-terminal fragment of human CRT, the amino acid sequence of which is residues 181-417 of SEQ ID NO:2; and
   (b) a second nucleic acid sequence that is linked in frame to said first nucleic acid sequence and encodes an antigenic polypeptide or peptide, wherein the antigenic polypeptide or peptide is selected from the group consisting of:
      i) a tumor-specific or tumor-associated antigen, or an antigenic epitope thereof, present on, or cross reactive with an antibody to an epitope of, a tumor cell;
      ii) an antigen of, or antigenic epitope thereof, or an antigen or antigenic epitope thereof cross-reactive with an antibody to an epitope of, a virus; and
      iii) an antigen of, or antigenic epitope thereof, or an antigen or antigenic epitope thereof cross-reactive with an antibody to an epitope of, a pathogenic organism.

2. The nucleic acid molecule of claim 1, wherein the antigenic peptide comprises an epitope that binds to a MHC class I protein.

3. The nucleic acid molecule of claim 2, wherein said epitope is between about 8 amino acid residues and about 11 amino acid residues in length.

4. The nucleic acid molecule of claim 1, wherein said CRT is human CRT comprising the amino acid sequence SEQ ID NO:2.

5. The nucleic acid molecule of claim 1, wherein the first nucleic acid sequence comprises the coding portion of SEQ ID NO: 1 or a fragment thereof, which fragment encodes:
   (i) an N-terminal fragment of human CRT, the amino acid sequence of which is residues 1-180 of SEQ ID NO:2; or
   (ii) a C-terminal fragment of human CRT, the amino acid sequence of which is residues 181-417 of SEQ ID NO:2.

6. The nucleic acid molecule of claim 1, wherein the antigenic polypeptide or peptide is an antigen or an antigenic epitope of a virus.

7. The nucleic acid molecule of claim 6, wherein the virus is a human papilloma virus.

8. The nucleic acid molecule of claim 7, wherein the antigenic polypeptide or peptide is the E7 polypeptide of HPV-16 or an antigenic fragment thereof.

9. The nucleic acid molecule of claim 6, wherein the antigenic polypeptide or peptide is a tumor-specific or tumor-associated antigen, or an antigenic epitope thereof.

10. An expression vector or cassette comprising the nucleic acid molecule of claim 1 operatively linked to
    (a) a promoter.

11. The expression vector or cassette of claim 10 which is a viral vector or a plasmid.

12. The expression vector or cassette of claim 10 which is a self-replicating RNA replicon.

13. The expression vector or cassette of claim 10 wherein the calreticulin polypeptide comprises amino acid sequence SEQ ID NO:2.

14. A particle suitable for introduction into a cell or an animal by particle bombardment comprising the nucleic acid of claim 1.

15. A pharmaceutical composition capable of inducing or enhancing an antigen-specific immune response, comprising:

(a) pharmaceutically and immunologically acceptable excipient in combination with;
(b) the nucleic acid molecule of claim 1.

16. A pharmaceutical composition capable of inducing or enhancing an antigen-specific immune response, comprising:
(a) pharmaceutically and immunologically acceptable excipient in combination with;
(b) the expression vector or cassette of claim 10.

17. The pharmaceutical composition of claim 15, wherein the CRT polypeptide comprises amino acid sequence SEQ ID NO:2.

18. A method of inducing or enhancing an antigen specific immune response in a subject comprising administering to the subject an effective amount of the pharmaceutical composition of claim 15, thereby inducing or enhancing said response.

19. The method of claim 18 wherein said administering is by a intramuscular, intradermal, or subcutaneous route.

20. The method of claim 18 wherein administering is by biolistic injection of said nucleic acid molecule.

21. A method of increasing the numbers or lytic activity of CD8$^+$ CTLs specific for a selected antigen in a subject, comprising administering to said subject an effective amount of the pharmaceutical composition of claim 15, wherein
(i) said nucleic acid molecule encodes said selected antigenic polypeptide or peptide, and
(ii) said selected antigenic polypeptide or peptide comprises an epitope that binds to, and is presented on the cell surface by, MHC class I proteins,
thereby increasing the numbers or activity of said CTLs.

22. A method of inhibiting growth or preventing re-growth of a tumor in a subject, comprising administering to said subject an effective amount of a pharmaceutical composition of claim 15, wherein said nucleic acid molecule encodes one or more tumor-associated or tumor-specific epitopes present on said tumor in said subject, thereby inhibiting said growth or preventing said re-growth.

23. The method of claim 22, further comprising before, together with or after said administering of said pharmaceutical composition, administering to said subject a second composition having anti-angiogenic activity.

24. The method of claim 21 wherein said administering is by a intramuscular, intradermal, or subcutaneous route.

25. The method of claim 21 wherein said administering is by biolistic injection of said nucleic acid molecule.

26. The method of claim 22 wherein said administering is by a intramuscular, intradermal, or subcutaneous route.

27. The method of claim 22 wherein said administering is by biolistic injection of said nucleic acid molecule.

28. The nucleic acid molecule of claim 1, wherein the first and the second nucleic acid sequences are fused in frame with a linker nucleic acid sequence encoding a linker peptide.

29. The expression vector or cassette of claim 10, further comprising additional regulatory sequences that regulate expression of said nucleic acid in a eukaryotic cell.

30. The method of claim 18, wherein said administering is by an intradermal route.

31. The method of claim 24, wherein said administering is by an intradermal route.

32. The method of claim 26, wherein said administering is by an intradermal route.

33. The nucleic acid molecule of claim 7, wherein the antigenic polypeptide or peptide is the E6 polypeptide of HPV-16 or an antigenic fragment thereof.

34. The pharmaceutical composition of claim 15, wherein the antigenic polypeptide or peptide is the E7 polypeptide of HPV-16, or an antigenic fragment thereof.

35. The pharmaceutical composition of claim 15, wherein the antigenic polypeptide or peptide is the E6 polypeptide of HPV-16, or an antigenic fragment thereof.

36. The method of claim 18, wherein the antigenic polypeptide or peptide is the E7 polypeptide of HPV-16, or an antigenic fragment thereof.

37. The method of claim 18, wherein the antigenic polypeptide or peptide is the E6 polypeptide of HPV-16, or an antigenic fragment thereof.

38. The method of claim 21, wherein the antigenic polypeptide or peptide is the E7 polypeptide of HPV-16, or an antigenic fragment thereof.

39. The method of claim 21, wherein the antigenic polypeptide or peptide is the E6 polypeptide of HPV-16, or an antigenic fragment thereof.

40. The method of claim 22, wherein the antigenic polypeptide or peptide is the 7 polypeptide of HPV-16, or an antigenic fragment thereof.

41. The method of claim 22, wherein the antigenic polypeptide or peptide is the E6 polypeptide of HPV-16, or an antigenic fragment thereof.

* * * * *

UNITED STATES PATENT AND TRADEMARK OFFICE
CERTIFICATE OF CORRECTION

| | | |
|---|---|---|
| PATENT NO. | : 7,342,002 B2 | Page 1 of 2 |
| APPLICATION NO. | : 10/343448 | |
| DATED | : March 11, 2008 | |
| INVENTOR(S) | : Tzyy-Choou Wu et al. | |

It is certified that error appears in the above-identified patent and that said Letters Patent is hereby corrected as shown below:

IN THE TITLE

Title Page, item [54] and col. 1 insert --RETICULUM-- after "ENDOPLASMIC".

IN THE CLAIMS

Claim 1 should read as follows:

--1. A nucleic acid molecule encoding a fusion polypeptide useful as an immunogenic or vaccine composition, which molecule comprises:

(a) a first nucleic acid sequence encoding a first polypeptide that is a calreticulin (CRT) polypeptide or an active CRT fragment which fragment is:

(i) an N-terminal fragment of human CRT, the amino acid sequence of which is residues 1-180 of SEQ ID NO:2; or (ii) a C-terminal fragment of human CRT, the amino acid sequence of which is residues 181-417 of SEQ ID NO:2; and (b) a second nucleic acid sequence that is linked in frame to said first nucleic acid sequence and encodes an antigenic polypeptide or peptide, wherein the antigenic polypeptide or peptide is selected from the group consisting of:

i) a tumor-specific or tumor-associated antigen, or an antigenic epitope thereof;

ii) an antigen or antigenic epitope of a virus; and iii) an antigen or antigenic epitope of a pathogenic micro-organism.--

UNITED STATES PATENT AND TRADEMARK OFFICE
CERTIFICATE OF CORRECTION

PATENT NO. : 7,342,002 B2
APPLICATION NO. : 10/343448
DATED : March 11, 2008
INVENTOR(S) : Tzyy-Choou Wu et al.

It is certified that error appears in the above-identified patent and that said Letters Patent is hereby corrected as shown below:

Col. 50 Claim 10 should read as follows:

--10. An expression vector or cassette comprising the nucleic acid molecule of claim 1 operatively linked to a promoter.--

Col. 50 Claim 13 should read as follows:

--13. The expression vector or cassette of claim 10 wherein, the calreticulin polypeptide comprises amino acid sequence SEQ ID NO:2.--

Col. 52 Claim 40 should read as follows:

--40. The method of claim 22, wherein the antigenic polypeptide or peptide is the E7 polypeptide of HPV-16, or an antigenic fragment thereof.--

Signed and Sealed this

Twenty-third Day of September, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,342,002 B2 |
| APPLICATION NO. | : 10/343448 |
| DATED | : March 11, 2008 |
| INVENTOR(S) | : Tzyy-Choou Wu et al. |

It is certified that error appears in the above-identified patent and that said Letters Patent is hereby corrected as shown below:

IN THE TITLE

Title Page, item [54] and col. 1 insert --RETICULUM-- after "ENDOPLASMIC".

IN THE CLAIMS

Column 49, Claim 1, lines 32-58 should read as follows:

--1. A nucleic acid molecule encoding a fusion polypeptide useful as an immunogenic or vaccine composition, which molecule comprises:

(a) a first nucleic acid sequence encoding a first polypeptide that is a calreticulin (CRT) polypeptide or an active CRT fragment which fragment is:

(i) an N-terminal fragment of human CRT, the amino acid sequence of which is residues 1-180 of SEQ ID NO:2; or (ii) a C-terminal fragment of human CRT, the amino acid sequence of which is residues 181-417 of SEQ ID NO:2; and (b) a second nucleic acid sequence that is linked in frame to said first nucleic acid sequence and encodes an antigenic polypeptide or peptide, wherein the antigenic polypeptide or peptide is selected from the group consisting of:

i) a tumor-specific or tumor-associated antigen, or an antigenic epitope thereof;

ii) an antigen or antigenic epitope of a virus; and iii) an antigen or antigenic epitope of a pathogenic micro-organism.--

UNITED STATES PATENT AND TRADEMARK OFFICE
CERTIFICATE OF CORRECTION

| | |
|---|---|
| PATENT NO. | : 7,342,002 B2 |
| APPLICATION NO. | : 10/343448 |
| DATED | : March 11, 2008 |
| INVENTOR(S) | : Tzyy-Choou Wu et al. |

It is certified that error appears in the above-identified patent and that said Letters Patent is hereby corrected as shown below:

Col. 50 Claim 10, lines 51-53 should read as follows:

--10. An expression vector or cassette comprising the nucleic acid molecule of claim 1 operatively linked to a promoter.--

Col. 50 Claim 13, lines 59-61 should read as follows:

--13. The expression vector or cassette of claim 10 wherein, the calreticulin polypeptide comprises amino acid sequence SEQ ID NO:2.--

Col. 52 Claim 40, lines 39-41 should read as follows:

--40. The method of claim 22, wherein the antigenic polypeptide or peptide is the E7 polypeptide of HPV-16, or an antigenic fragment thereof.--

This certificate supersedes the Certificate of Correction issued September 23, 2008.

Signed and Sealed this

Fourteenth Day of October, 2008

JON W. DUDAS
*Director of the United States Patent and Trademark Office*